US011596680B2

(12) United States Patent
Cobb et al.

(10) Patent No.: US 11,596,680 B2
(45) Date of Patent: Mar. 7, 2023

(54) NOROVIRUS VACCINE

(71) Applicant: RESILIENCE GOVERNMENT SERVICES, INC., La Jolla, CA (US)

(72) Inventors: Ron Cobb, Gainesville, FL (US); Michael Springer, Foxborough, MA (US); Yawei Ni, College Station, TX (US)

(73) Assignee: RESILIENCE GOVERNMENT SERVICES, INC., Alachua, FL (US)

( * ) Notice: Subject to any disclaimer, the term of this patent is extended or adjusted under 35 U.S.C. 154(b) by 0 days.

(21) Appl. No.: 16/877,015

(22) Filed: May 18, 2020

(65) Prior Publication Data

US 2020/0345828 A1 Nov. 5, 2020

Related U.S. Application Data

(62) Division of application No. 15/754,807, filed as application No. PCT/US2016/048940 on Aug. 26, 2016, now abandoned.

(60) Provisional application No. 62/211,289, filed on Aug. 28, 2015.

(51) Int. Cl.
| *A61K 39/12* | (2006.01) |
| *A61K 39/295* | (2006.01) |
| *A61K 9/16* | (2006.01) |
| *A61K 9/19* | (2006.01) |
| *A61K 9/00* | (2006.01) |
| *A61K 39/00* | (2006.01) |

(52) U.S. Cl.
CPC ............ *A61K 39/12* (2013.01); *A61K 9/0095* (2013.01); *A61K 9/1694* (2013.01); *A61K 9/19* (2013.01); *A61K 39/00* (2013.01); *A61K 39/295* (2013.01); *A61K 2039/5258* (2013.01); *A61K 2039/541* (2013.01); *A61K 2039/55583* (2013.01); *A61K 2039/70* (2013.01); *C12N 2770/16023* (2013.01); *C12N 2770/16034* (2013.01); *C12N 2770/16071* (2013.01)

(58) Field of Classification Search
None
See application file for complete search history.

(56) References Cited

U.S. PATENT DOCUMENTS

| 6,777,000 | B2 | 8/2004 | Ni et al. |
| 7,494,669 | B2 | 2/2009 | Ni et al. |
| 7,705,135 | B2 | 4/2010 | Ni et al. |
| 8,074,906 | B2 | 12/2011 | Talton |
| 2007/0207526 | A1 | 9/2007 | Coit et al. |
| 2010/0266636 | A1* | 10/2010 | Richardson ............ A61P 31/14 424/216.1 |
| 2013/0095134 | A1 | 4/2013 | Arntzen et al. |
| 2018/0243397 | A1 | 8/2018 | Cobb et al. |

FOREIGN PATENT DOCUMENTS

| CN | 101848704 A | 9/2010 |
| CN | 101918028 A | 12/2010 |
| CN | 102177233 B | 4/2015 |
| CN | 104583393 A | 4/2015 |
| CN | 104740624 A | 7/2015 |
| JP | 2005-506284 | 3/2005 |
| JP | 2005532987 A | 11/2005 |
| JP | 2010505766 A | 2/2010 |
| JP | 2010539192 A | 12/2010 |
| WO | WO 02/067897 | 9/2002 |
| WO | WO 2009/039229 | 3/2009 |
| WO | WO 2008/042789 | 4/2009 |
| WO | WO 2011/079260 | 6/2011 |
| WO | WO 2013/192604 | 12/2013 |
| WO | WO 2015/004995 | 1/2015 |
| WO | WO-2017040265 A1 | 3/2017 |

OTHER PUBLICATIONS

Sundararajan, A. et al. "Robust mucosal-homing antibody-secreting B cell responses induced by intramuscular administration of adjuvanted bivalent human norovirus-like particle vaccine" *Vaccine*, 2015, 33:568-576.
Lobue, A.D. et al. "Multivalent norovirus vaccines induce strong mucosal and systemic blocking antibodies against multiple strains," *Vaccine*, 2006, 24:5220-5234.

(Continued)

*Primary Examiner* — Nicole Kinsey White
(74) *Attorney, Agent, or Firm* — Wilson Sonsini Goodrich & Rosati

(57) ABSTRACT

A dry powder norovirus vaccine is provided, which comprises at least two norovirus antigens representing different genogroups. The vaccine may be produced by formulation with a mixture of different antigens or combination of monovalent powders with each containing one antigen. The formulated vaccine is suitable for mucosal administration and soluble in aqueous solutions for parenteral administration. A method of immunization is also provided, which comprises at least one administration of the vaccine via mucosal and/or parental route. The immunization may have multiple administrations of the vaccine, i.e., one or more immunizations via a mucosal route followed by one or more immunizations via a parenteral route or vice versa, to maximize both mucosal and systemic immune responses and protection against norovirus infections.

13 Claims, 17 Drawing Sheets

(56) References Cited

OTHER PUBLICATIONS

Ball, J. P. et al. "Intranasal delivery of a bivalent norovirus vaccine formulated in an in situ gelling dry powder" *PLoS ONE*, 2017, pp. 1-16, vol. 12, No. 5, e0177310.
Velasquez, L. S. et al. "Intranasal delivery of Norwalk virus-like particles formulated in an in situ gelling, dry powder vaccine" *Vaccine*, 2011, pp. 5221-5231, vol. 29, No. 32.
Debbink, K. et al. "The State of Norovirus Vaccines" *Clin. Infectious Dis.*, 2014, 58(12):1746-1752.
EP16842675.7 Extended European Search Report dated Jul. 1, 2019.
PCT/US2016/048940 International Search Report and Written Opinion dated Jan. 17, 2017.
U.S. Appl. No. 15/754,807 Office Action dated Jun. 21, 2019.
U.S. Appl. No. 15/754,807 Office Action dated Dec. 19, 2019.
Atmar et al. Determination of the 50% Human Infectious Dose for Norwalk Virus. The Journal of Infectious Diseases 2014:209, pp. 1016-1022 (Apr. 1, 2014). Electronically published Nov. 18, 2013.
Atmar et al. Norovirus Vaccine against Experimental Human Norwalk Virus Illness. N Engl J Med 2011;365:2178-87.
Atmar et al. Serological Correlates of Protection against a GII.4 Norovirus. Clin Vaccine Immunol, vol. 22, No. 8, pp. 923-929 (Aug. 2015). Accepted manuscript posted online Jun. 3, 2015.
Bernstein et al. Norovirus Vaccine Against Experimental HumanGII.4 Virus Illness: A Challenge Study in Healthy Adults. J Infect Dis 2015:211, pp. 870-878 (Mar. 15, 2015). Electronically published Sep. 9, 2014.
Blanton et al. Molecular and Epidemiologic Trends of Caliciviruses Associated with Outbreaks of Acute Gastroenteritis in the United States, 2000-2004. The Journal of Infectious Diseases 2006; 193:413-21. Electronically published Dec. 21, 2005.
Bok et al. Chimpanzees as an animal model for human norovirus infection and vaccine development. PNAS, vol. 108, No. 1, pp. 325-330 (Jan. 4, 2011).
Caul. Small round structured viruses: airborne transmission and hospital control. The Lancet, vol. 343, pp. 1240-1242 (May 21, 1994).
Czakó et al. Experimental Human Infection with Norwalk Virus Elicits a Surrogate Neutralizing Antibody Response with Cross-Genogroup Activity. Clin Vaccine Immunol 22:221-228 (2015). Accepted manuscript posted online Dec. 24, 2014.
Donaldson et al. Norovirus pathogenesis: mechanisms of persistence and immune evasion in human populations. Immunol Rev, vol. 225, pp. 190-211 (2008).
Fankhauser et al. Epidemiologic and Molecular Trends of "Norwalk-like Viruses" Associated with Outbreaks of Gastroenteritis in the United States. The Journal of Infectious Diseases 2002;186:1-7. Electronically published Jun. 10, 2002.
Hall et al. Norovirus Disease in the United States. Emerging Infectious Diseases, vol. 19, No. 8, pp. 1198-1205 (Aug. 2013).
Hansman et al. Genetic and antigenic diversity among noroviruses, Journal of General Virology (2006), 87, 909-919.
Harrington et al. Binding of Norwalk Virus-Like Particles to ABH Histo-Blood Group Antigens Is Blocked by Antisera from Infected Human Volunteers or Experimentally Vaccinated Mice. Journal of Virology, vol. 76, No. 23, pp. 12335-12343 ( Dec. 2002).
Hedberg. Food-Related Illness and Death in the United States. Emerg Infect Dis, vol. 5, No. 6, pp. 840-841 (Nov.-Dec. 1999).
Herbst-Kralovetz et al. Norwalk virus-like particles as vaccines. Expert Rev Vaccines. Mar. 2010 ; 9(3): 299-307.
Karst. Pathogenesis of Noroviruses, Emerging RNA Viruses. Viruses 2, 748-781 (Mar. 23, 2010).
Koho et al. Purification of norovirus-like particles (VLPs) by ion exchange chromatography. Journal of Virological Methods 181 (2012) 6-11. Available online Jan. 14, 2012.
Lindesmith et al. Broad Blockade Antibody Responses in Human Volunteers after Immunization with a Multivalent Norovirus VLP Candidate Vaccine: Immunological Analyses from a Phase 1 Clinical Trial. PLoS Med 12(3): e1001807 (Mar. 24, 2015). 32 pages.
Lindesmith et al. Emergence of a Norovirus GII.4 Strain Correlates with Changes in Evolving Blockade Epitopes. Journal of Virology, vol. 87, No. 5, pp. 2803-2813 (Mar. 2013). Published ahead of print Dec. 26, 2012.
Lindesmith et al. Monoclonal Antibody-Based Antigenic Mapping of Norovirus GII.4-2002. Journal of Virology, vol. 86, No. 2, p. 873-883 (Jan. 2012). Published ahead of print Nov. 16, 2011.
Marionneau et al. Norwalk Virus Binds to Histo-Blood Group Antigens Present on Gastroduodenal Epithelial Cells of Secretor Individuals. Gastroenterology 2002;122:1967-1977.
Mead et al. Food-Related Illness and Death in the United States—Reply to Dr. Hedberg. Emerg Infect Dis, vol. 5, No. 6, pp. 841-842 (Nov.-Dec. 1999).
Norovirus. Centers for Disease Control and Prevention (CDC). Retrieved Oct. 10, 2022 at URL: https://www.cdc.gov/norovirus/. 2 pages.
Parker et al. Identification of Genogroup I and Genogroup II Broadly Reactive Epitopes on the Norovirus Capsid. Journal of Virology, vol. 79, No. 12, pp. 7402-7409 (Jun. 2005).
Parra et al. Immunogenicity and Specificity of Norovirus Consensus GII.4Virus-like Particles in Monovalent and Bivalent Vaccine Formulations. Vaccine. May 21, 2012; 30(24): 3580-3586.
Patel et al. Systematic Literature Review of Role of Noroviruses in Sporadic Gastroenteritis. Emerging Infectious Diseases, vol. 14, No. 8, pp. 1224-1231 (Aug. 2008).
Reeck et al. Serological Correlate of Protection against Norovirus-Induced Gastroenteritis. The Journal of Infectious Diseases 2010; 202(8):1212-1218. Electronically published Sep. 3, 2010.
Sakon et al. Impact of Genotype-Specific Herd Immunity on the Circulatory Dynamism of Norovirus: A 10-Year Longitudinal Study of Viral Acute Gastroenteritis. J Infect Dis 2015:211, pp. 879-888 (Mar. 15, 2015). Electronically published Sep. 9, 2014.
Santi et al. An efficient plant viral expression system generating orally immunogenic Norwalk virus-like particles. Vaccine. Mar. 28, 2008; 26(15): 1846-1854.
Santi et al. Virus like particles production in green plants. Methods. Sep. 2006 ; 40(1): 66-76.
Springer et al. Preclinical Dose Ranging Studies of a Novel Dry Powder Norovirus Vaccine Formulation. Vaccine. Mar. 14, 2016; 34(12): 1452-1458.
Tacket et al. Humoral, mucosal, and cellular immune responses to oral Norwalk virus-like particles in volunteers. Clinical Immunology 108 (2003) 241-247.
Treanor et al. A Novel Intramuscular Bivalent Norovirus Virus-Like Particle Vaccine Candidate—Reactogenicity, Safety, and Immunogenicity in a Phase 1 Trial in Healthy Adults. The Journal of Infectious Diseases 2014;210:1763-71. Electronically published Jun. 20, 2014.
Vesikari et al. Norovirus Vaccine: One Step Closer. J Infect Dis 2015:211, pp. 853-855 (Mar. 15, 2015). Electronically published Sep. 9, 2014.
White et al. Biochemical characterization of a smaller form of recombinant Norwalk virus capsids assembled in insect cells. Journal of Virology, vol. 71, No. 10, pp. 8066-8072 (Oct. 1997).
Yun et al. Complete genome sequence and phylogenetic analysis of a recombinant Korean norovirus, CBNU1, recovered from a 2006 outbreak. Virus Research 152 (2010) 137-152. Available online Jun. 25, 2010.
Zheng et al. Molecular Epidemiology of Genogroup II-Genotype 4 Noroviruses in the United States between 1994 and 2006. Journal of Clinical Microbiology, vol. 48, No. 1, pp. 168-177 (Jan. 2010).

* cited by examiner

A.

B.

A.

B.

A.

B.

Western blot

A.

B.

A.

B.

A.

B.

A.

B.

A.

B.

A.

B.

A.

B.

C.

D.

A.

B.

C.

D.

A.

B.

A.

B.

C.

D.

NOROVIRUS VACCINE

CROSS REFERENCE TO RELATED APPLICATIONS

This application is a divisional of U.S. application Ser. No. 15/754,807, filed Feb. 23, 2018, which is the National Stage of International Application PCT/US2016/048940, filed Aug. 26, 2016, which claims priority to U.S. Provisional Patent Application 62/211,289, filed Aug. 28, 2015, the entire disclosure of which is incorporated by reference herein.

FIELD OF INVENTION

The present invention is generally related to vaccines for prevention of infectious diseases and more specifically a vaccine for prevention and/or alleviation of norovirus infections and norovirus-related diseases and symptoms.

BACKGROUND

Norovirus, a single-stranded RNA virus in the Caliciviridae family, is the primary cause of nonbacterial gastroenteritis worldwide, accounting for 96% of all cases of viral gastroenteritis [1]. It is estimated, on average, that norovirus is responsible for 19 to 21 million infections per year [2] and up to 200,000 deaths in children under 5 years of age in developing countries [3, 4]. Norovirus is transmitted primarily through the fecal-to-oral route [5] making norovirus particularly threatening to individuals who occupy a high density, communal environments such as schools, nursing homes, cruise ships, and in the military [6]. Norovirus is also stable ex vivo which makes decontamination after an outbreak laborious and time consuming. The robustness of norovirus, along with a low infectious dose (<10 virions per individual) [7], makes norovirus a highly infectious virus with dramatic socio-economic impacts. This disease burden strongly indicates the need for an effective vaccine; however, currently there is no FDA-approved norovirus vaccine available.

Norovirus is distributed among at least five different genogroups GI, GII, GIII, GIV, and GV. Only genogroups I, II, and IV are infectious to humans, with GI and GII being most prevalent [8, 9]. Recently, genogroup II has become the most prevalent, accounting for 81.4% of norovirus outbreaks worldwide [10]. Each genogroup is subdivided further into genoclusters. Full-length genomic sequencing of various norovirus strains indicate that norovirus can vary by 3% to 31% within genogroups and 49% to 54% between genogroups [11]. Due to this wide variation, development of a broadly effective vaccine remains a challenge as the antibodies from humans immunized against one genogroup do not cross react with noroviruses from other genogroups [12].

The success of virus-like particles (VLPs) as vaccine antigens has been demonstrated by the licensure of hepatitis B virus VLP and human papilloma-virus VLP vaccines. Extensive research has focused on the development of norovirus VLPs as vaccine antigens that can be delivered parenterally, orally, or mucosally [13, 14]. Clinical evidence has demonstrated that norovirus VLPs administered orally or intranasally were well tolerated and modestly immunogenic [15, 16]. Additional studies have employed recombinant expression techniques to produce norovirus VLPs using baculovirus and tobacco mosaic virus, demonstrating that VLPs can be produced in a commercial scale with comparable structure and immunogenicity of norovirus VLPs produced in a traditional way [18, 19].

Previous studies have shown that administration of norovirus VLPs through the nasal cavity is able to induce systemic immunity as well as both local and distal mucosal immunity [20, 21]. Furthermore, the incorporation of norovirus VLPs with GELVAC nasal dry powder formulation elicits a greater immune response than antigen alone [20]. GELVAC is the dry powder formulation with GELSITE, which is an *Aloe vera* L.-derived polysaccharide polymer with mucoadhesive properties. In the presence of divalent cations, GELVAC is capable of in-situ gelation which improves mucosal residence time of intranasally administered vaccines [22].

Although previous studies have shown promises of norovirus VLPs as a potential vaccine, there is still a great need to produce a norovirus vaccine that is multivalent, targeting the wide variation of norovirus strains. Moreover, the vaccine should be suitable for multiple routes of administrations in order to minimize the number of invasive injections. In addition, a vaccine in a form a dry power is preferred over a traditional liquid form as a dry powder can be stably stored at a room temperature for a long period.

SUMMARY OF INVENTION

The present invention relates to formulations of a dry powder norovirus vaccine comprising one, two or more antigens from different genogroups of noroviruses. In some embodiments, the norovirus vaccine formulation is monovalent, comprising genogroup GII VLP antigens. In some embodiment, the norovirus vaccine formulation is multivalent, containing multiple norovirus VLP antigens derived from multiple genogroups of norovirus. In certain embodiments, the vaccine formulation is a multivalent norovirus vaccine comprising two norovirus VLP antigens from GI and GII noroviruses, respectively. In certain embodiments, the vaccine formulation is a multivalent norovirus vaccine comprising three norovirus VLP antigens from GI, GII and GIV noroviruses respectively. In some embodiments, norovirus VLP antigens are recombinant VLPs. Recombinant norovirus virus-like particles are obtained by expressing the virus-like particles in an expression system selected from a group consisting of viruses, baculovirus expression systems, tobacco mosaic virus vector systems, prokaryotic cells, *E. coli* systems, yeast (*S. cerevisiae*), eukaryotic expression systems, Sf9 insect cells, mammalian cells, HEK 293 and CHO cells.

Formulations of a dry powder norovirus vaccine may further comprise anionic polysaccharide. In some embodiments, anionic polysaccharide is sodium polygalacturonate. Sodium polygalacturonate is an *Aloe vera* L.-derived polysaccharide polymer with mucoadhesive properties. In the presence of divalent cations, the dry powder formulation of this compound improves mucosal residence time of administered vaccines. In some embodiments, a formulation of a dry powder norovirus vaccine is produced as one powder formulation with a mixture of two or more norovirus VLP antigens. In another embodiment, the vaccine is formulated as a combination of two or more monovalent vaccine powders with each containing one norovirus VLP antigen.

The present invention further provides methods of producing a dry powder norovirus vaccine that is multivalent. The methods may include a lyophilization-milling method. In another embodiment, the methods comprise a spray-drying method. In some embodiments, the sodium polygalacturonate comprises at least 0.1% (w/w). In some embodiments, the norovirus virus-like particle comprises about 1 μg to 100 μg of the vaccine formulation.

The present invention further provides methods of immunization against norovirus infections which comprises at least one immunization via a parenteral and/or a mucosal route. In some embodiments, one or more immunizations via a mucosal route is followed by one or more immunizations via a parenteral route or vice versa, to maximize both mucosal and systemic immune responses and protection against norovirus infection. In some embodiments, a dry powder vaccine is used for both parenteral and mucosal immunizations, i.e., the mucosal immunization is performed directly with the dry powder vaccine by intranasal delivery, whereas the parenteral immunization with the reconstituted dry powder vaccine by intramuscular (IM) injection. An increase in norovirus specific antibodies and norovirus neutralizing antibodies in the subject following immunization is indicative of active immunity against norovirus in the subject.

DETAILED DESCRIPTION OF THE INVENTION

Figure 1:
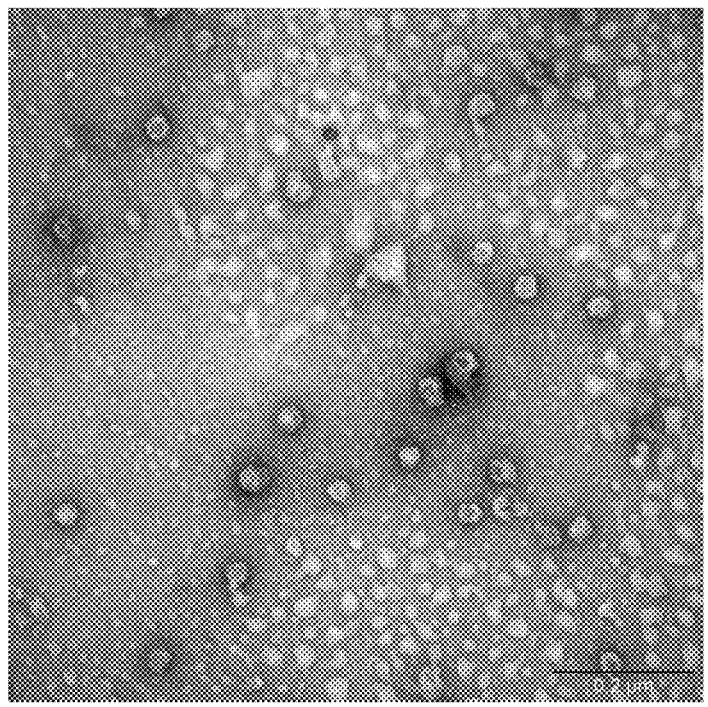
FIG. 1: Transmission electron microscopy of norovirus VLPs. GI (A) and GII.4 (B) VLPs were dissolved in water and imaged at 150,000× magnification (scale bar 100 μm). VLP particles were spherical in appearance at the expected size of 23 nm to 38 nm.
Figure 1:
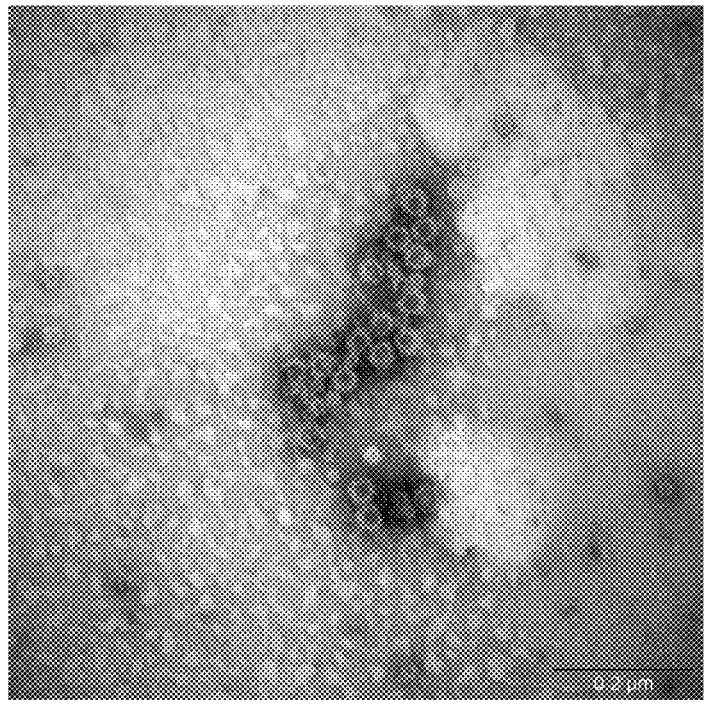

The present invention includes formulations of a norovirus vaccine in a form of a dry powder, methods of producing such vaccine, and methods of performing immunization by administering such vaccine.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

The articles "a" and "an," as used herein, should be understood to mean "at least one," unless clearly indicated to the contrary. The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Norovirus

The present invention provides a formulation comprising at least two norovirus virus-like particle antigens. "Norovirus" herein refers to members of the genus Norovirus of the family Caliciviridae. In some embodiments, norovirus includes a group of viruses that cause acute gastroenteritis in human and can be infectious to mammals including, but not limited to, human. Norovirus may include at least five genogroups (GI-GV) defined by nucleic acid and amino acid sequences known in the art [40]. In some embodiments, norovirus refers to a subset of genogroups. In certain embodiment, norovirus refers to GI and GII. genogroups. In certain embodiments, norovirus refers to GI, GII and GIV genogroups.

A number of examples of norovirus is known in the art. The examples include, but not limited to, Norwalk virus, Southampton virus, Desert Shield virus, and Hawaii virus. New strains of norovirus are routinely discovered [41]. Use of a combination of norovirus genogroups such as GI and GII or synthetic constructs representing combinations or portions thereof are considered in some embodiments.

Norovirus may refer to recombinant norovirus virus-like particles (VLPs). Norovirus VLPs are structurally similar and immunogenic as native norovirus, but lack the viral RNA genome of norovirus that is required for infection. "Virus-like particles" or "VLPs" herein refer to virus-like particles or fragments thereof, produced using methods known in the art [18, 19]. In some embodiments, VLPs are produced using baculovirus or tobacco mosaic virus [18, 19, 23].

"Norovirus antigen" or "antigen" herein refers to any form of proteins or peptides of norovirus VLPs and fragments thereof, that elicit immune response in vivo. Norovirus VLPs may contain norovirus capsid proteins or fragments thereof such as, but not limited to, VP1 and VP2. In some embodiments, norovirus antigen comprises norovirus VLPs. In some embodiments, norovirus VLPs may be monovalent or multivalent. As used herein, "monovalent" refers to antigens derived from a single genogroup of norovirus. "Multivalent" refers to antigens derived from two or more genogroups of norovirus. For example, if the formulation used herein is referred as multivalent, the formulation comprises antigens derived from different genogroups of norovirus. When norovirus VLPs are multivalent, norovirus VLPs may have capsid proteins or derivatives such as VP1 and VP2 from different genogroups of norovirus. A combination of monovalent or multivalent norovirus VLPs may be used in a formulation of a norovirus vaccine. In those embodiments, the resulting vaccine is referred as multivalent, comprising norovirus VLPs derived from different genogroups of norovirus. A multivalent vaccine is bivalent, when it comprises two norovirus VLPs from two different genogroups; trivalent, when it comprises three norovirus VLP from three different genogroups.

Antigen Preparation

As used herein, antigens may be isolated and purified from organisms as naturally occurred. Antigens may be produced by recombinant techniques. For example, norovirus VLPs can be produced from cells such as prokaryotic or eukaryotic cells. Those cells include, but not limited to, *E. coli, S. cerevisiae*, insect cells such as Sf9, and mammalian cells such as HEK293 cells and CHO cells. In some embodiments, an antigen is a recombinant norovirus VLP derived from GI and/or GII genogroups. The recombinant norovirus VLPs may be expressed using baculovirus or tobacco mosaic virus [18, 19]. In some embodiments, recombinant norovirus VLPs are expressed and produced from plants such as *Nicotiana benthamiana*, as described previously [23]. Briefly, clarified leaf extracts containing norovirus VLPs are filtered and concentrated. The extracts further run through a sepharose column, allowing the recovery of the VLPs. Endotoxins and other impurities may be further removed by a fractionation. In some embodiments, the purity of norovirus VLPs is at least 80%, 85%, 90%, 95%, 98%, 99%, 99.5%, or 100%. Norovirus VLPs as used herein preferably do not interfere with the efficacy of each VLP to elicit immunogenicity in vivo when used in combination.

Vaccine Formulation

As used herein, "vaccine" or "vaccine formulation" refers to a formulation containing norovirus antigens that can be administered to mammals including human and elicit immune response in vivo. The vaccine formulation of this invention may prevent and/or ameliorate an infection of norovirus. The vaccine formulation may reduce at least one symptom related to norovirus infection. The vaccine formulation may further enhance the efficacy of another dose of norovirus antigen. As used herein, "immunogenicity," "immunogenic response," or "immune response" refers to humoral and/or cell-mediated immune response. Humoral response leads to production of antibodies from B lymphocytes. Cell-mediated immune response refers to response mediated by T lymphocytes or other cells such as macrophages.

In some embodiments, norovirus vaccine is formulated as a form of a dry powder, capable of being administered by a mucosal route. In some embodiments, the dry powder vaccine is delivered via an intranasal way using an intranasal delivery device. The dry powder vaccine formulation may be administered as a dry powder form or optionally be reconstituted in an aqueous solution prior to administration to mammals. Thus, the vaccine formulation may be soluble in an aqueous solution. The aqueous solution includes, but not limited to, water and saline buffer. Other routes to administer the vaccine formulation are considered in some embodiments, and include, but not limited to, dermal and parenteral methods. In some embodiments, the vaccine is delivered by intramuscular injection. Detailed routes and options to administer the formulation of the present invention will be discussed in immunization methods section.

The present invention includes a formulation of norovirus vaccine that is monovalent or multivalent. A multivalent norovirus vaccine may be formulated as one powder formulation containing one multivalent norovirus VLP antigen, or at least two monovalent or multivalent norovirus VLP antigens. Alternatively, the multivalent vaccine may be formulated as a mixture of at least two dry powder formulations, each containing one monovalent or multivalent norovirus VLP antigen. Thus, norovirus vaccine as used herein may comprise one or more norovirus VLP antigens derived from different genogroups of norovirus. In certain embodiments, norovirus vaccine comprises two norovirus VLP antigens derived from different genogroups of norovirus. In those embodiments, norovirus VLPs may be derived from GI and GII. Norovirus VLPs may be present from 0.01 μg to 1,000 μg per 20 mg of dry powder vaccine formulation, depending on the desired dose. In some embodiments, norovirus VLPs are 10 μg to 50 μg per 20 mg of dry powder vaccine formulation.

A formulation of norovirus vaccine as used herein may further comprise at least one or more excipients. Excipients used in the formulation preferably do not interfere with norovirus VLPs. In some embodiments, the excipient further enhances the therapeutic efficacy of the vaccine formulation by increasing mucosal residence time of administered vaccine formulation. The formulation of the present invention may comprises at least one or more excipients categorized in the type of including, but not limited to, preservatives, viscosity adjusting agents, tonicity adjusting agents, and buffering agents.

The formulation in a form of a dry powder may also contain one or more excipients. In some embodiments, the vaccine formulation comprises a polymer with mucoadhesive properties. In certain embodiments, the vaccine formulation comprises anionic polysaccharides. Anionic polysaccharides include, but not limited to, dextran, guar gum, ben gum, methyl cellulose, and sodium polygalacturonate. In some embodiments, the vaccine formulation comprises sodium polygalacturonate and/or GELSITE. GELSITE is a chemically and functionally distinct high molecular weight anionic polysaccharide (sodium polygalacturonate) extracted from an *Aloe vera* L. An exemplary method to extract a polymer from *Aloe vera* L. as used herein is incorporated as a reference (U.S. Pat. No. 7,705,135). Sodium polygalacturonate and GELSITE may be used herein interchangeably. The dry powder vaccine formulation may contain GELSITE in amounts of at least 0.01%, 0.1%, 0.25%, 0.5%, or 1% (w/w). In certain embodiments, the dry powder vaccine formulation contains 0.25% (w/w) of GELSITE. "GELVAC norovirus vaccine" refers to a dry powder vaccine formulation comprising GELSITE and at least one norovirus VLP antigen.

Because the formulation of the present invention may comprise one or more excipients with mucoadhesive properties, the formulation may not require immune adjuvants such as alum adjuvants. In some embodiments, the vaccine formulation may further comprise excipients such as, but not limited to, povidone and lactose. Povidone (polyvinylpyrrolidone) is routinely used in the pharmaceutical industry as a synthetic polymer vehicle for dispersing and suspending drugs. Lactose is also a commonly used excipient in the pharmaceutical industry.

Production Methods

Norovirus vaccine formulation of the present invention may be produced as a form of a dry powder and stored anhydrous until it is ready to be used. Various methods to dry a formulation are known in the art [42]. The methods include, but not limited to, precipitation, crystallization, jet milling, spray-drying and lyophilizing (freeze-drying). Downstream operations may be further required, such as drying, milling and sieving. In some embodiments, the formulation can be freeze-dried, producing powders with desirable characteristics. Cryo-milling may be further required in order to produce a homogenous mixture. An exemplary lyophilized-milling method is incorporated herein as a reference (U.S. Pat. No. 8,074,906). Alternatively, the formulation may be produced as a powder by a spray-drying method. Once it is in a form of a dry powder, norovirus vaccine may have an average diameter particle size from 1 μm to 100 μm.

In some embodiments, at least two norovirus VLP antigens derived from different genogroups of norovirus are added in the formulation in order to produce a multivalent dry powder norovirus vaccine. In some embodiments, at least three norovirus VLP antigens from different norovirus genogroups are added in the formulation in order to produce a multivalent dry powder vaccine. In another embodiment, a multivalent dry powder norovirus vaccine is generated by mixing at least two dry powders, each containing one norovirus VLP antigen. Drying constitutes desiccating, dehydrating, or substantially dehydrating the formulation, such that a dry powder formulation is prepared. In some embodiments, each dried formulation may be milled using a mortar and pestle under a controlled, low-humidity (<10% RH) environment, and the formulation is optionally passed through a 70 μm filter to sterilize the formulation.

Immunization Methods

The amount of antigen in each antigenic or vaccine formulation dose is selected as an amount which induces a robust immune response without significant, adverse side effects. In general, the dose administered to a subject, in the context of the present invention should be sufficient to effect a beneficial therapeutic response in the subject over time, or to induce the production of antigen-specific antibodies. Thus, the vaccine formulation is administered to a patient in an amount sufficient to elicit an immune response to the specific antigens and/or to alleviate, reduce, or cure symptoms and/or complications from the disease or infection. An amount adequate to accomplish this is defined as a "therapeutically effective dose."

The vaccine formulation of the present invention may be administered through such as, but not limited to, mucosal, dermal, and parenteral routes. Exemplary detailed routes further include, but not limited to, oral, topical, subcutaneous, intranasal, intravenous, intramuscular, intranasal, sublingual, transcutaneous, subdermal, intradermal, and suppository routes. The vaccine formulation may be administered as a form of a dry power or reconstituted in an aqueous solution prior to administration. In some embodiments, at least two immunizations are given to a subject at once or separated by a few hours, days, months, or years. In some embodiments, one or more immunizations are administered by a mucosal route or a parenteral route. In some embodiments, one or more immunizations via a mucosal route is followed by one or more immunizations via a parenteral route or vice versa, to maximize both mucosal and systemic immune responses and protection against norovirus infection. In some embodiments, a dry powder vaccine is used for both parenteral and mucosal immunizations, i.e., the mucosal immunization is performed directly with the dry powder vaccine by intranasal delivery, whereas the parenteral immunization with the reconstituted dry powder vaccine by intramuscular injection.

As mentioned above, the vaccine formulation of the invention may be administered to a subject to reduce the risk of norovirus infection prior to any future exposure to norovirus, ameliorate and/or treat symptoms of norovirus infection. Symptoms of norovirus infection are well known in the art and include, but not limited to, nausea, vomiting, diarrhea, stomach cramping, a low-grade fever, headache, chills, muscle aches, and fatigue. The invention encompasses a method of inducing an immune response in a subject not exposed to norovirus at the time of administration of the vaccine formulation of this invention. Alternatively, the formulation may be administered to a subject currently experiencing a norovirus infection such that at least one symptom associated with norovirus infection is alleviated and/or reduced after administration. Successful immunization with the vaccine confers an active immunity against norovirus in the immunized subject. A therapeutically effective dose for immunizing a subject with the vaccine is one that results in the generation of specific antibodies against the vaccinated antigen. Additionally, a therapeutically effective dose for immunizing a subject with the vaccine is one that results in increase in norovirus neutralizing antibodies in the subject. Increase in specific antibodies against norovirus antigens in the serum and mucosa of the subject confers active immunity. Similarly, generation of norovirus neutralizing antibody in the subject confers active immunity against a norovirus infection. Increase in the titer of specific antibody is usually proportional to the degree of protective immunity conferred by the vaccine. A reduction in a symptom may be determined subjectively or objectively, e.g., self-assessment by a subject, by a clinician's assessment or by conducting an appropriate assay or measurement including, but not limited to, body temperature, a level of norovirus infection, antibody titer, and T cell counts.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Example 1

GI and GII Vaccine Formulation

Recombinant norovirus GI and GII VLPs expressed in *Nicotiana benthamiana* were obtained from Kentucky Bioprocessing (Owensboro, Ky.) as previously described [23] and used for powder formulations. Alternatively, recombinant Norovirus GI and GII VLPs expressed and purified from Sf9 insect cells using the baculovirus expression system were also used [18, 19].

The GELVAC vaccine powders were made with a lyophilization-milling method. Liquid formulations were first prepared using a formulation that is comprised of the recombinant VLP in a solution with GELSITE polymer, povidone and lactose. They were then lyophilized. Following lyophilization, dried formulation contain 0.25% (w/w) GELSITE, 99% lactose and 0.05% povidone and 0 µg to 100 µg (based on ELISA data) of VLP per 20 mg of formulation, depending on the desired dose. The GI and GII VLPs were added together to the formulation to produce the multivalent powder or individually to produce the monovalent powders. The multivalent powder can also be produced by mixing together two or more monovalent powders. Each dried formulation could be milled using a mortar and pestle under a controlled, low-humidity (<10% RH) environment and passed through a 70 µm filter. The powder formulations can be made using a spray-drying apparatus as well. Powders were stored in sealed containers under desiccation at room temperature until use.

Example 2

Characterization of Vaccine Formulations

VLP Characterization

GI and GII VLP stocks were analyzed for the presence of intact VLPs by transmission electron microscopy prior to powder manufacturing. The results confirmed the presence of intact VLPs of the expected sizes (38 nm) for both GI and GII VLP stocks (FIG. 1).

Figure 2:
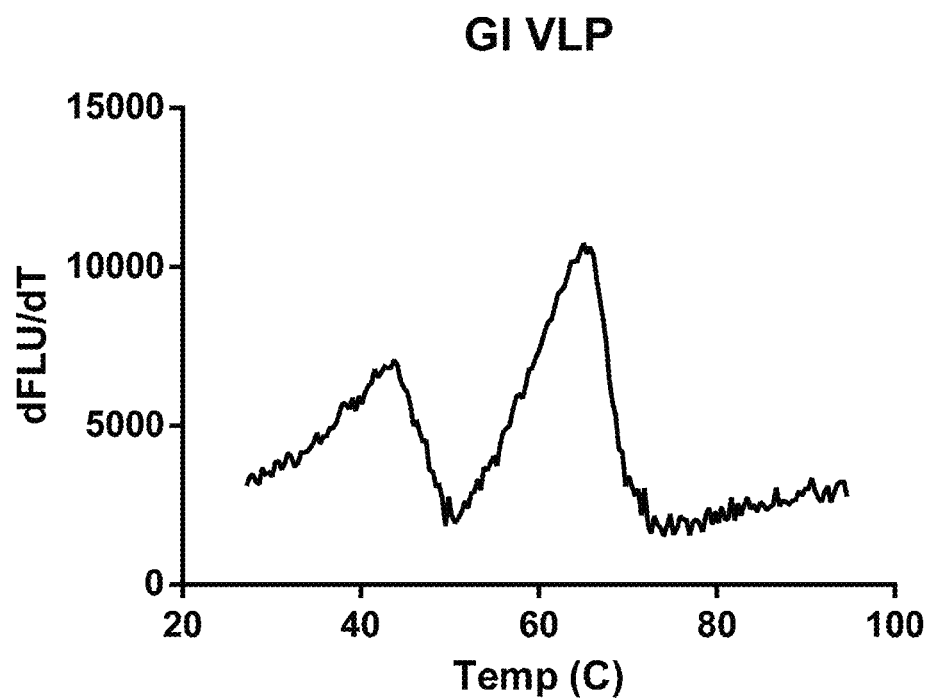
FIG. 2: Thermal stability evaluation of norovirus VLPs using SYPRO Orange. VLPs were diluted in 4×SYPRO orange solution and the melt curve was analyzed using a fluorescent thermocycler. Data is plotted as the change in Fluorescence per unit Temperature. A. Norovirus GI VLP melt curve. B. Norovirus GII.4 VLP melt curve.
Figure 2:
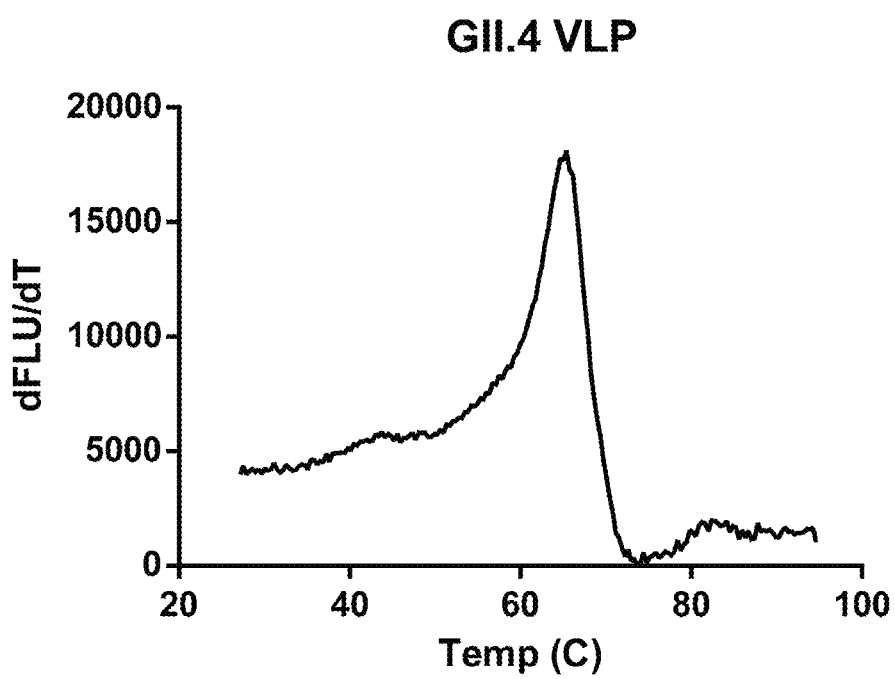

VLP stability was established by determining the melt temperature of norovirus VLPs with SYPRO Orange. Briefly, SYPRO Orange (Sigma-Aldrich, St. Louis, Mo.) was diluted in PBS to make a final 4× concentration of SYPRO Orange. Each VLP was diluted in 4×SYPRO Orange to a final concentration of 1 mg/mL. Each sample was then placed in a fluorescent thermocycler and was run through a 25° C.-95° C. gradient while reading the fluorescent signal. The derivative of the signal was determined by taking the difference between successive points in the fluorescent signal. The noise was reduced by using a 4-point moving average filter. Melt curve plots are shown for GI (FIG. 2A) and GII (FIG. 2B). GI VLPs had two melt peaks, one minor peak at 43° C. and a major peak at 65° C. GII VLPs showed a major peak at 65° C. The major peak observed in the GII VLP melt curve is consistent with the major peak for GI VLPs. These results demonstrated that the VLP antigens were stable at temperatures up to 65° C.

VLP stability was also evaluated based on antigenicity. Norovirus VLPs were incubated at various temperatures and tested in a capture ELISA. Mouse monoclonal IgG2 anti-norovirus antibodies (Maine Biotech, MAB228 (GI); MAB227 (GII)) diluted 1:2000 in PBS were coated on Nunc MaxiSorp 96-well plates (Fisher Scientific, Pittsburgh, Pa.) overnight at 4° C. The wells were washed 5 times with wash buffer, and then blocked for 1 hr at room temperature in blocking buffer. Norovirus VLPs were diluted in blocking buffer, and allowed to incubate on the plate at room temperature for 1 hr. The wells were washed 3 times with wash buffer, followed by incubation with corresponding mouse monoclonal IgG1 anti-norovirus antibodies (Millipore, MAB80143 (GI); Maine Biotech MAB226 (GII)) diluted 1:2000 in blocking buffer for 1 hr at room temperature. The wells were washed 3 times with wash buffer, followed by incubation with a polyclonal anti-mouse IgG1:HRP (Abcam, Cambridge, Mass.) diluted 1:2000 in blocking buffer for 1 hr at room temperature. Finally, the wells were washed 3 times with wash buffer and were developed using 1-step Ultra TMB according to manufacturer's protocol (Thermo Scientific, Waltham, Mass.). The OD at 450 nm was measured and plotted against known VLP concentrations.

Figure 3:
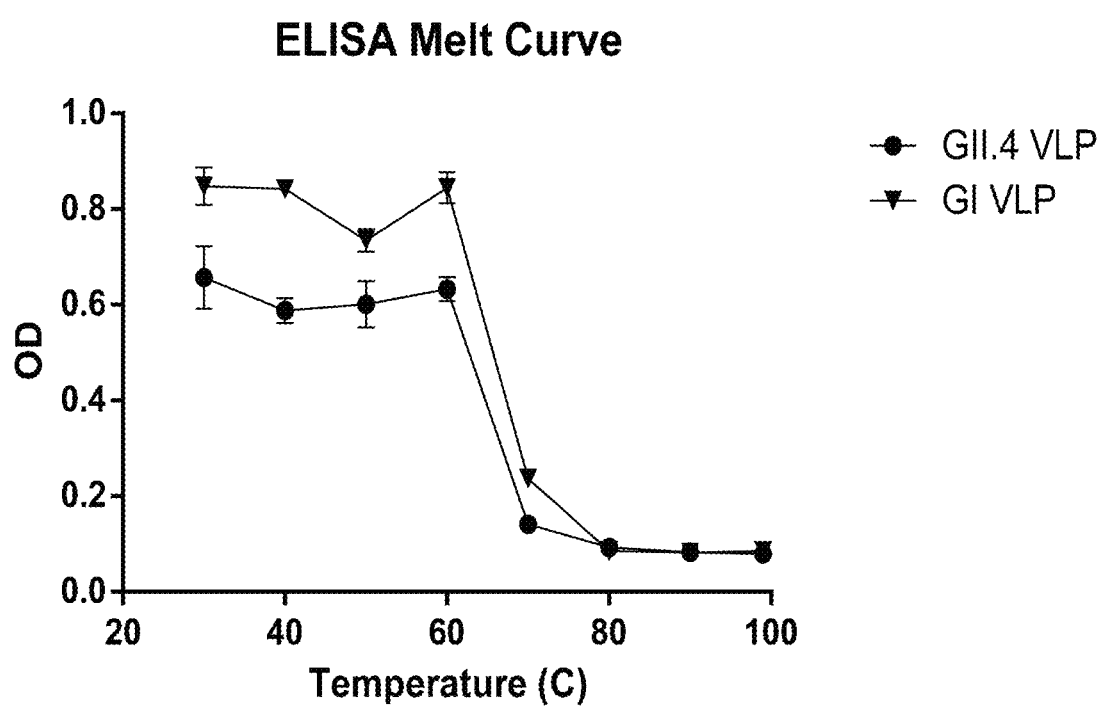
FIG. 3: Thermal stability evaluation of norovirus VLPs using capture ELISA. VLP samples (0.2 μg/mL) were treated at varying temperatures for 5 minutes. Each sample was then analyzed by capture ELISA.

For each VLP, the OD decreased significantly at 65° C., consistent with the major melt peaks observed via SYPRO Orange (FIG. 3). Thus, the denaturing of the VLP antigens at high temperatures was correlated with the loss of antigenicity. These results also confirm the specificity of the capture ELISA to intact VLPs, which was used to determine the antigen dose content of each GELVAC vaccine powder for use in the animal studies.

GELVAC Vaccine Powder Characterization

The GELVAC vaccine powder was manufactured through a manual milling process under nitrogen gas. Laser diffraction particle size distribution confirmed the volumetric mean particle size to be 24 µm to 37 µm for all powders, which was determined using a laser diffraction particle size analyzer with a liquid module (Beckman Coulter LS13 320, Pasadena, Calif.). Furthermore, the d10 for the powders was approximately 5 µm for all powders, thus minimizing the amount of powders (<5 µm) which can reach deep lung. A representative particle distribution result for each antigen can be found in Table 1. The mean particle diameter for the GI VLP formulation was 29.73 µm and for GII VLP formulation was 25.2 µm.

TABLE 1

Representative volumetric particle size distribution of GI and GII monovalent vaccine powders

| Vaccine powders | Mean | d10 | d50 | d90 |
|---|---|---|---|---|
| GI | 29.73 µm | 5.08 µm | 25.23 µm | 59.25 µm |
| GII | 25.20 µm | 5.49 µm | 22.97 µm | 49.32 µm |

Figure 4:
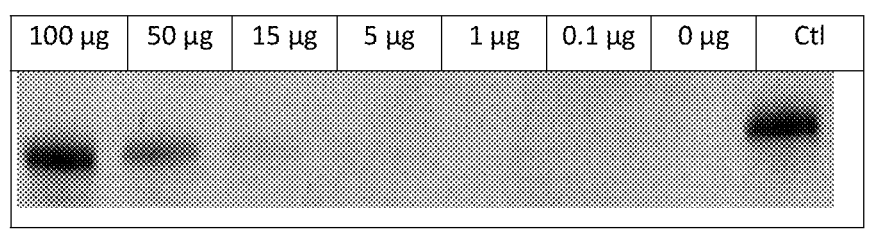
FIG. 4: SDS-PAGE and western blot analysis of GELVAC GI (A) and GII.4 (B) vaccine powders. Vaccine powders were reconstituted and analyzed by SDS-PAGE and western blot to confirm the presence of VLPs. Order from left to right: 100 μg, 50 μg, 15 μg, 5 μg, 1 μg, 0.1 μg, 0, reference standard. Both GI and GII had observable bands at ~55 kDa, consistent with the size of VP1 capsid protein.
Figure 4:
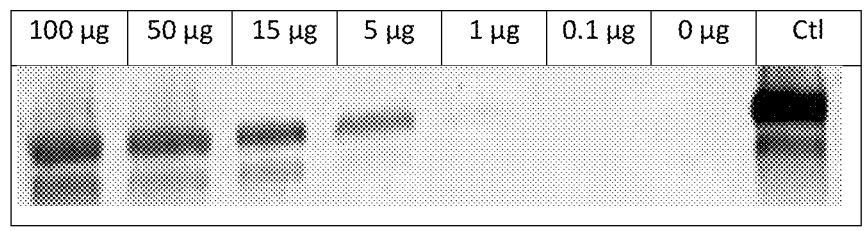
Figure 4:
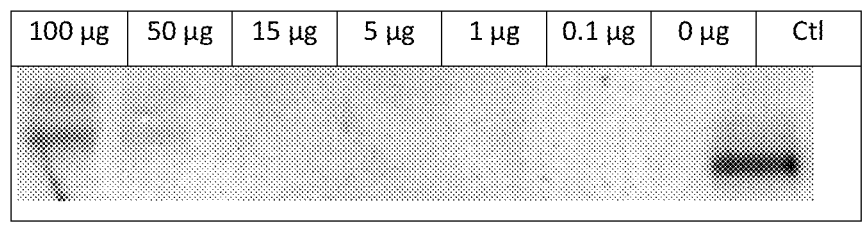
Figure 4:
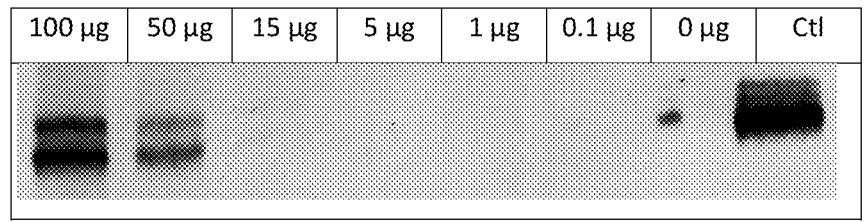

To determine the presence of norovirus VP1 for each GI and GII in the vaccine powders, SDS-PAGE and western blotting was performed (FIG. 4). Both SDS-PAGE and western blotting show the presence of a major band at ~55 kDa in all powders. These results are consistent with the expected size of VP1. Due to the lack sensitivity, VLPs were not visible in doses <15 µg in either SDS-PAGE or western blot. The multiple bands present have been observed previously and confirmed to be due to possible truncation of the VP1 protein [26, 27]. These results also show relative amounts of VP1 were consistent with total VLP concentration.

Capture ELISAs were used to quantify the VLP dose content of each vaccine powder. GI and GII capture ELISAs were performed with a 15 µg dose formulated vaccine. 10 mg of each 15 µg VLP dose powders were dissolved in 1 mL of water. Each powder was tested in the capture ELISA and compared to the VLP reference standard. Using a 4-PL fit, the antigen concentration of each powder was then quantified based on the weight of vaccine powder (Table 2). The capture ELISA was established using the GI- and GII-specific monoclonal antibodies. No cross-reactivity was observed between these two genogroups. In addition, no interference was observed with the powder formulation excipients.

TABLE 2

Testing of GELVAC GI and GII vaccine powders for antigen content

| Vaccine Powders | Expected Antigen Dose (µg VLP/mg Powder) | Observed Antigen Dose (µg VLP/mg Powder) |
|---|---|---|
| GI VLP | 15 µg/10 mg | 15.46 µg/10 mg |
| GII VLP | 15 µg/10 mg | 16.16 µg/10 mg |

Example 3

Immunogenicity of Vaccine Formulations

Immunogenicity of GELVAC GI and GII Powders

The immunogenicity of a GELVAC vaccine powder formulated with GI VLP has been reported previously [20]. To further these studies, antigen dose-dependent immune responses were investigated with GELVAC vaccine powders with GI or GII VLPs in female (250 g) Hartley guinea pigs. Animals were dosed with varying amounts of norovirus GI or GII VLPs (Table 3) or with a multivalent GI/GII VLP vaccine (50 µg each of GI and GII VLP, twice on days 0 and 21.

TABLE 3

Monovalent Vaccine Animal Experimental Design
Monovalent Guinea Pig Studies

| Group # | n | Total Antigen per Vaccination (µg)* |
|---|---|---|
| 1 | 4 | 100 |
| 2 | 4 | 50 |
| 3 | 4 | 15 |
| 4 | 4 | 5 |
| 5 | 4 | 1 |
| 6 | 4 | 0.1 |
| 7 | 4 | 0 |

*Animals were immunized with a total of 20 mg of powder via both nares. Each nare received 10 mg of powder or half of the total antigen dose.

The vaccine powders were administered intranasally using Aptar Unit Dose Spray (UDS) Devices (Aptar Pharma, Congers, N.Y.), one per nare with half of the total antigen dose per nare (10 mg total powder per nare). The control group was administered the same amount of a placebo powder formulation. Serum and vaginal lavage samples were collected from the animals on days 0 (preimmunization), 21, 42 and 56.

Clinical Observations

There were no abnormal clinical findings in the guinea pigs after vaccination. There were also no statistical differences in body weight between the control and test vaccine groups (data not shown). Throughout the 56 day duration of the immunogenicity study, all vaccines were well tolerated by the test subjects. One animal in the 100 µg dose group for GI antigen was lost after the second immunization on day 21. Upon autopsy examination, death was attributed to anesthesia and/or the blood collection procedure.

Serum Antibody Response

Serum samples were analyzed for norovirus VLP specific IgG by ELISA. Norovirus GI or GII VLPs (2 µg/mL) in PBS were incubated on Nunc MaxiSorp 96-well plates (Fisher Scientific) for 4 hrs at room temperature. The plates were blocked overnight at 4° C. in blocking buffer. All samples were diluted in blocking buffer and serially diluted 2-fold down the plate. Samples were allowed to incubate at room temperature for 1 hr. The wells were washed 5 times with wash buffer, followed by incubation with anti-guinea pig IgG-HRP secondary antibodies (Southern Biotech, Birmingham, Ala.) at 1:1000 for 1 hr at room temperature. The wells were washed 5 times with wash buffer. The wells were developed using 1-step Ultra TMB according to manufacturer's protocol. End-point titers were reported as the reciprocal of the highest dilution that produced an OD of 0.1 above background. A positive control serum generated in guinea pigs against GI or GII VLP was included in each test run to confirm reproducibility.

Figure 5:
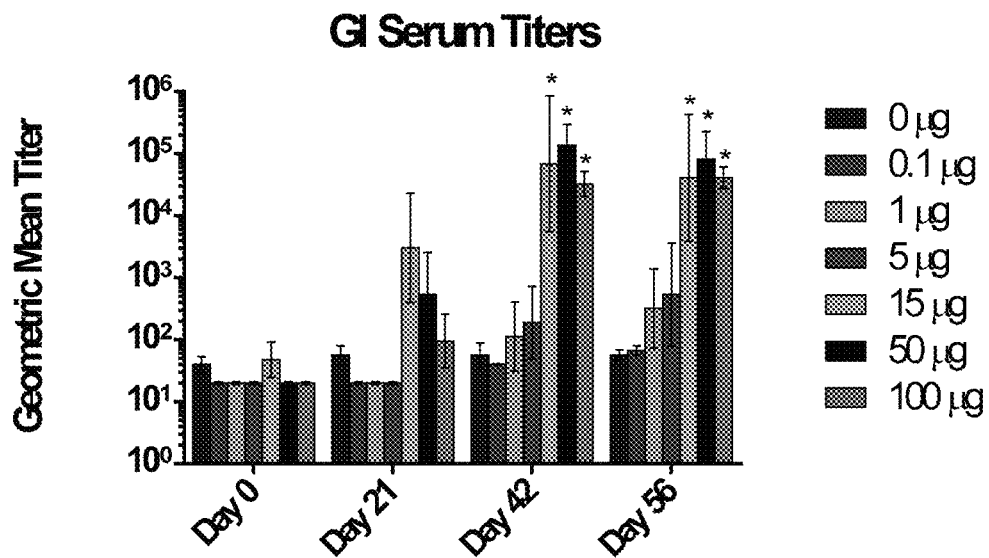
FIG. 5: Serum norovirus-specific IgG production following intranasal immunization with GELVAC vaccine powder. Female Hartley guinea pigs were immunized intranasally with 20 mg of powder formulation containing various amounts of VLP on days 0 and 21. Serum samples were collected on days 0, 14, 21, 42, and 56 and analyzed for GI (A) and GII.4 (B) Norovirus-specific IgG antibodies. *$P<0.05$ as compared to the placebo control group.
Figure 5:
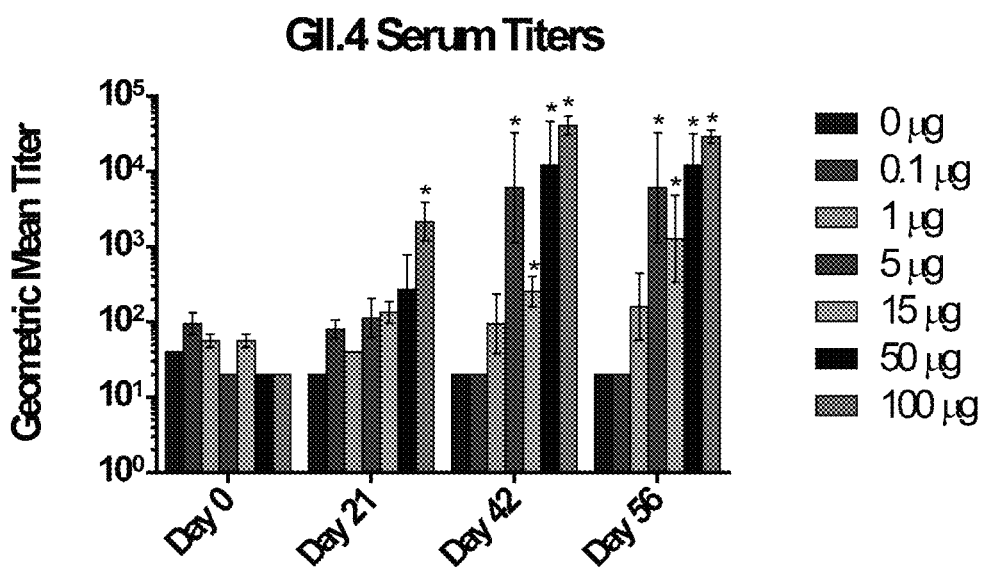
Figure 6:
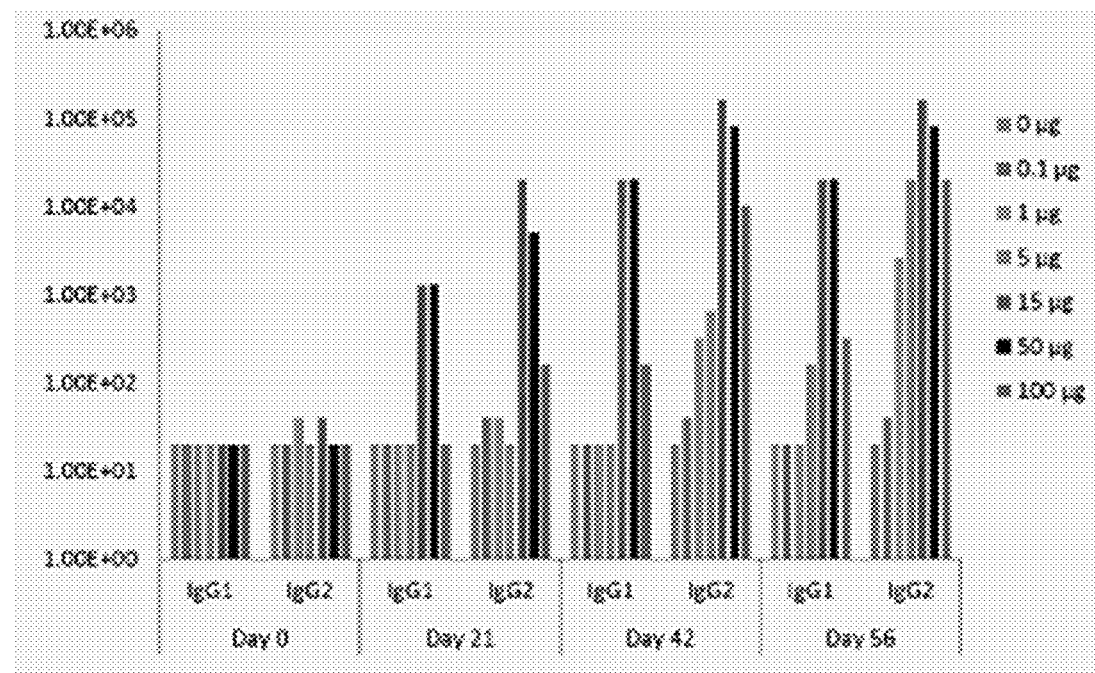
FIG. 6: Serum norovirus-specific IgG1 and IgG2 production following intranasal immunization with GELVAC vaccine powder. Female Hartley guinea pigs were immunized intranasally with 20 mg of powder formulation containing various amounts of VLP on days 0 and 21. Serum samples were collected on days 0, 14, 21, 42, and 56 and analyzed for GI (A) and GII.4 (B) Norovirus-specific IgG1 and IgG2 antibodies.
Figure 6:
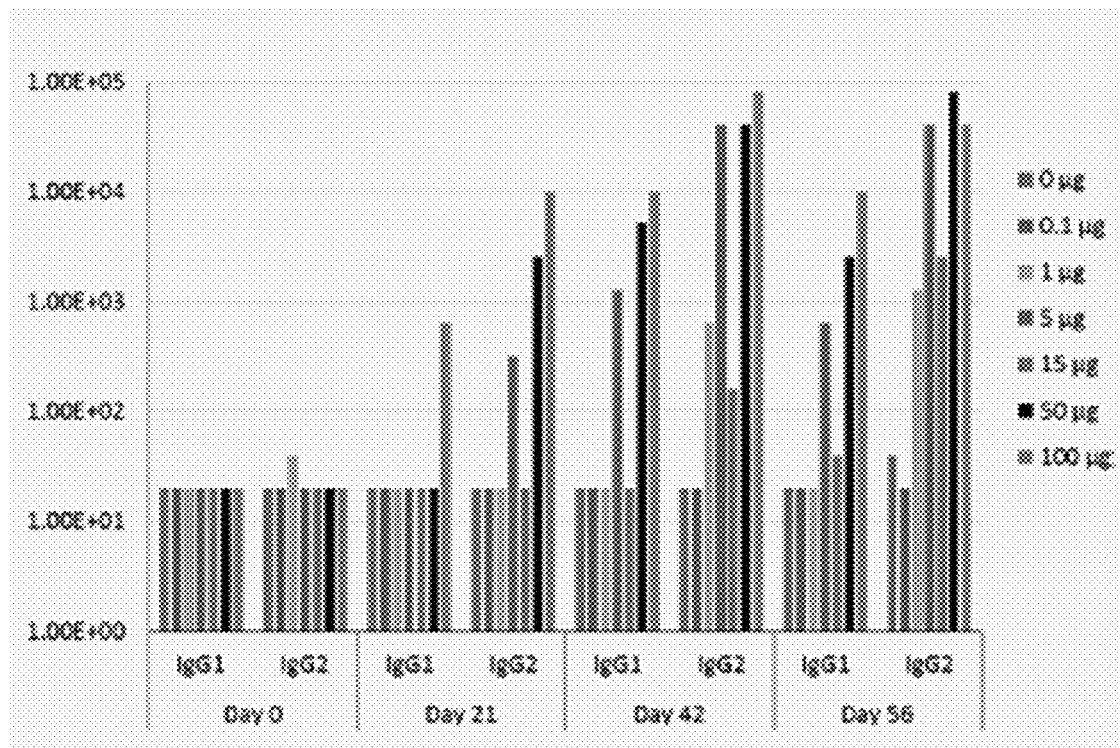
Figure 7:
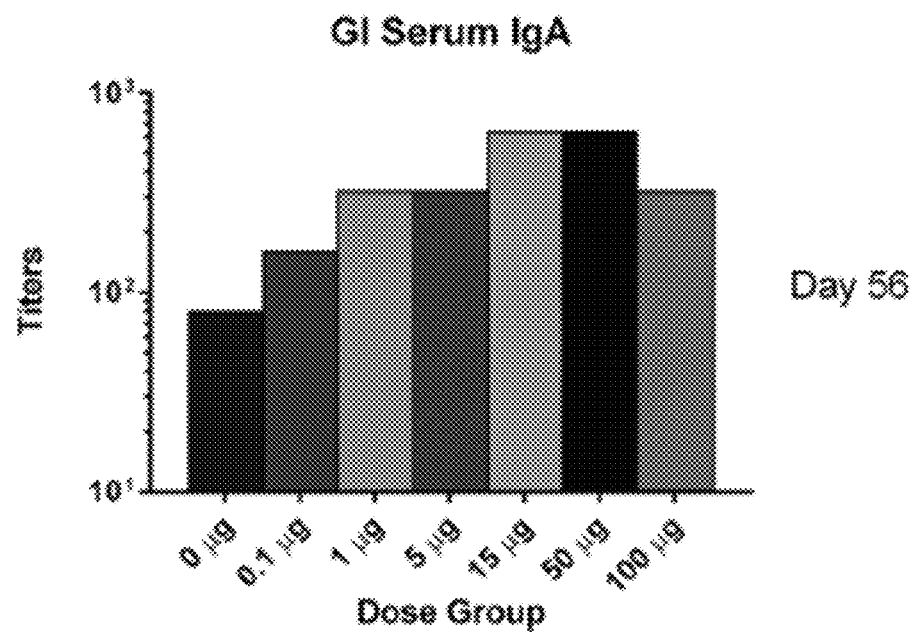
FIG. 7: Serum norovirus specific IgA production following intranasal immunization with GELVAC vaccine powder. Female Hartley guinea pigs were immunized intranasally with 20 mg of powder formulation containing various amounts of VLP on days 0 and 21. Serum samples were collected on day 56 and analyzed for GI (A) and GII.4 (B) Norovirus-specific IgA antibodies.
Figure 7:
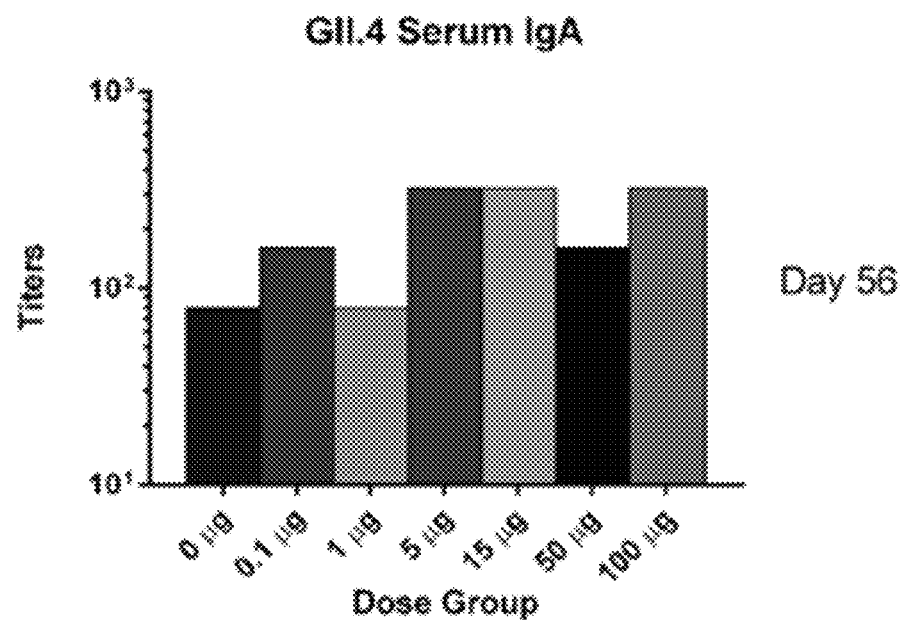
Figure 8:
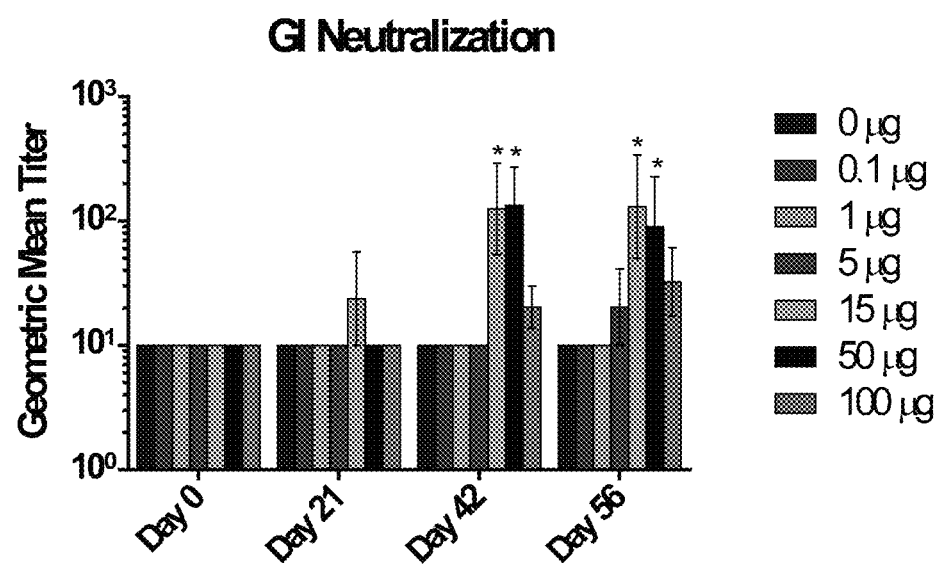
FIG. 8: Neutralizing antibody production following intranasal immunization with GELVAC vaccine powder. Female Hartley guinea pigs were immunized intranasally with 20 mg of powder formulation containing various amounts of VLP on days 0 and 21. Serum samples were collected on days 0, 14, 21, 42, and 56 and analyzed for GI (A) and GII.4 (B) neutralizing antibodies. *$P<0.05$ as compared to the placebo control group.
Figure 8:
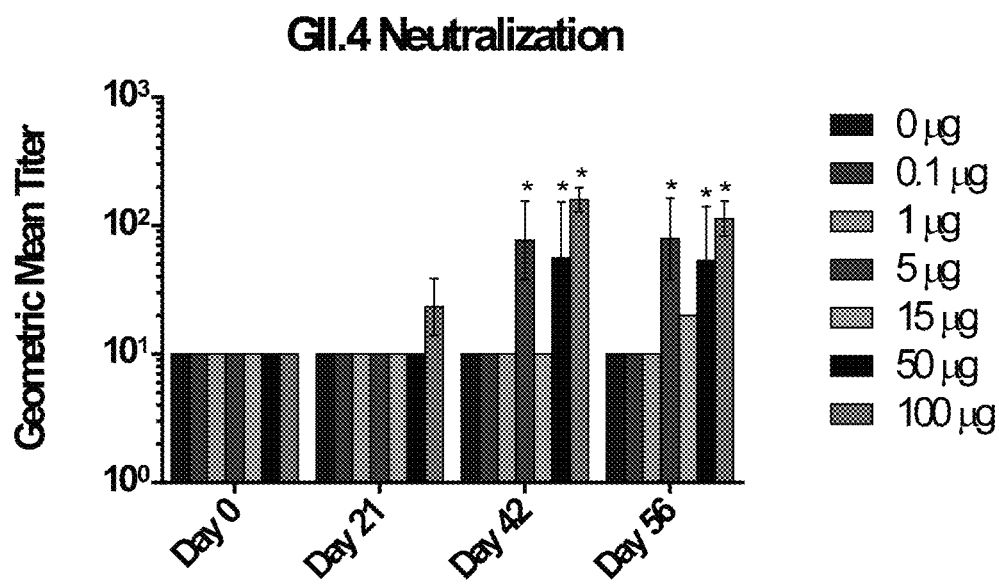
Figure 9:
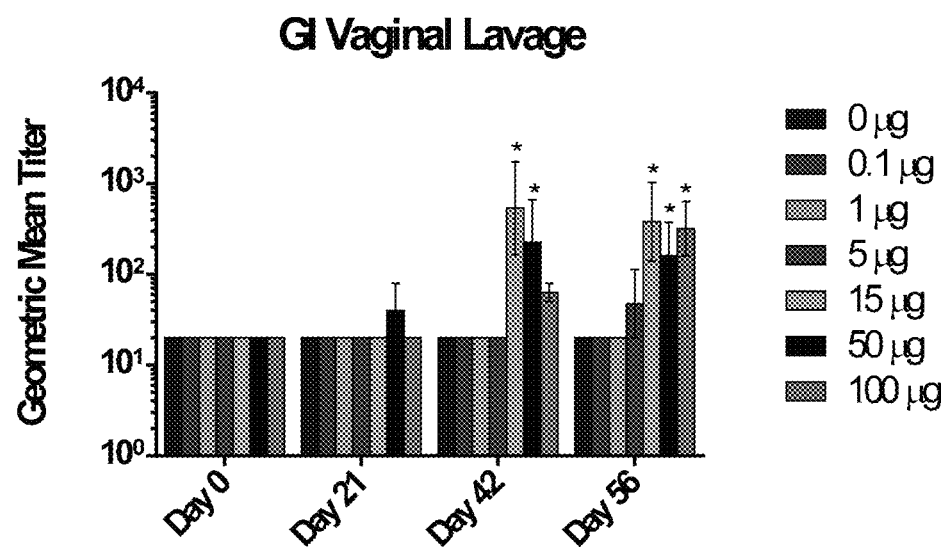
FIG. 9: Vaginal Norovirus-specific IgG production following intranasal immunization with GELVAC vaccine powder. Female Hartley guinea pigs were immunized intranasally with 20 mg of powder formulation containing various amounts of VLP on days 0 and 21. Vaginal lavages samples were collected on days 0, 14, 21, 42, and 56 and analyzed for GI (A) and GII.4 (B) Norovirus-specific IgG antibodies. *$P<0.05$ as compared to the placebo control group.
Figure 9:
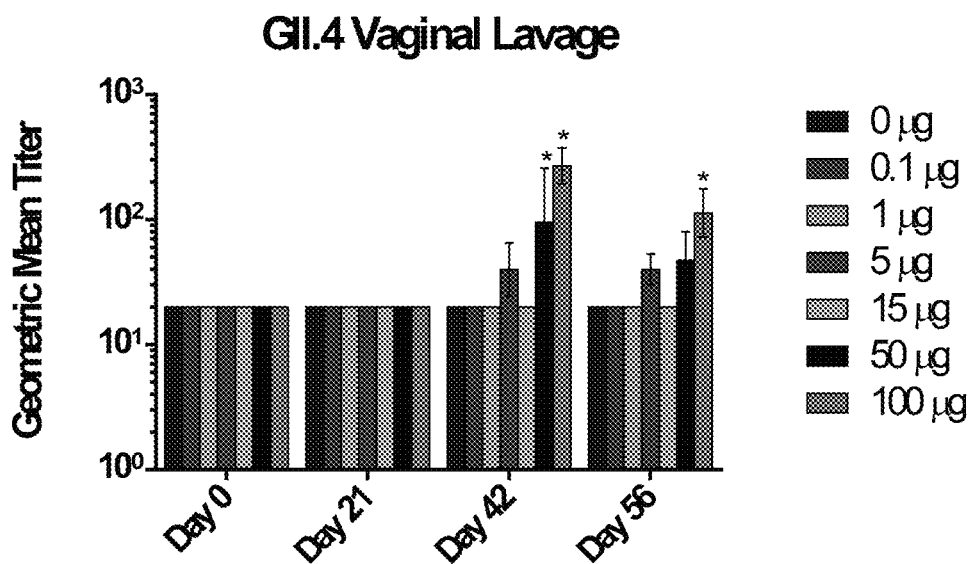

The total antigen specific IgG antibodies present in the serum exhibited a dose-dependent increase with both GI and GII vaccine powders (FIG. 5). Compared to the control group, serum IgG titers increased on day 21 and peaked by day 42 at all doses greater than 1 µg. By day 42, GI IgG titers increased by >600-fold for all dose groups of ≥15 µg and GII IgG titers increased by >300-fold for all dose groups of ≥5 µg. A dose of the vaccine which corresponds to >100-fold increase in antigen-specific IgG titers in the subject confers active immunity against a norovirus infection. An increase in antigen-specific antibody titer between 10- to 1000-fold is indicative of active immunity against the virus. There were no significant differences between 15 µg and 100 µg doses for GI and between 5 µg and 100 µg doses for GII. The lowest dose that elicited an antigen specific IgG response was 1 µg for both GI and GII which corresponded to a titer of 495 and 320 on day 56, respectively. As expected, all doses above 0.1 µg exhibited a boosting effect after the second dosing on day 21 with both GI and GII powders. These results showed that the VLPs formulation with GELVAC nasal powder were highly immunogenic and significant antibody production can be induced with GELVAC nasal powders with GI VLP at 15 µg and GII VLP at 5 µg.

Overall, both GI and GII vaccine powders induced a dose dependent antibody response. Serum antigen specific IgG antibody production was correlated with amounts of both GI and GII VLP antigens present in the powders and reached a maximal level at 15 μg to 50 μg of VLP antigen. Administration of higher doses of VLPs did not result in significantly higher levels of antigen specific IgGs. It is important to note that the boosting effect on systemic and mucosal IgGs was observed for each VLP antigen after the second dose on day 21.

Both IgG1 and IgG2 subclasses were also analyzed using the serum samples from each group (FIG. 6). Both IgG1 and IgG2 exhibited similar response profiles as the total IgG described above. The IgG2 titers were apparently higher than IgG1 titers with both GI and GII VLP powders, especially at low dose levels (1 and 5 μg) with a difference of up to 100 fold (FIG. 6).

Antigen-specific IgA serum levels were also investigated. At day 56, anti-GI and anti-GII VLP IgA antibodies were observed at all doses that were administered when compared to mock dose controls, except for the 1.0 μg dose group with GII (FIG. 7). They also showed an overall trend of higher levels at higher antigen doses. These results showed that the VLP formulations with GELVAC nasal powder were highly immunogenic and significant antigen specific antibody can be induced with GELVAC nasal powders with GI at 15 μg and GII VLP at 5 μg.

Serum Neutralization Antibody Response

Previous studies have demonstrated that norovirus VLP-specific antibodies can block the binding of norovirus VLP to ABH histo-blood group antigen (HBGA) in a strain specific manner [28]. HBGAs are carbohydrates ubiquitously expressed on mucosal tissues and red blood cells that have been implicated as natural receptors for norovirus binding and entry, demonstrating that blockade of HBGA interactions with VLPs may prevent norovirus infection [29]. To this end, antigen specific antibodies were investigated for their ability to inhibit the binding of the norovirus VLPs to porcine gastric mucin. The neutralizing antibodies present in the serum exhibited a dose-dependent response similar to that observed for antigen specific IgG antibody titers (FIG. 8). Compared to the control, GI neutralizing antibody titers were elevated in 15 μg dose group by day 21, in 15 μg, 50 μg, and 100 μg dose groups by day 42, and in all dose groups greater than 1 μg by day 56. GII neutralizing antibody titers were elevated for the 100 μg dose group by day 21, elevated by day 42 in the 5 μg, 50 μg, and 100 μg dose groups, and elevated in all dose groups greater than 1 μg by day 56. By day 42, GI neutralizing antibody titers increased by >5-fold for all dose groups of >5 μg and GII neutralizing antibody titers increased by >10-fold for all dose groups >1 μg, consistent with the findings with serum IgG titers. There were no significant differences between 5 μg and 100 μg doses for both GI and GII at day 56. The lowest dose that produced a detectable neutralization titer at day 56 was 5 μg for both GI and GII. The highest neutralizing antibody titers at day 56 occurred in the 15 μg dose group for GI and 100 μg dose group for GII. As expected, all groups above 5 μg for both GI and GII exhibited a boosting effect after the second dose on day 21. These results showed that the neutralizing antibody titers followed a similar dose-dependent response to that observed for the total serum IgG titers.

Production of antigen specific serum antibodies is necessary but not sufficient for protection against norovirus infection. However, production of serum antibodies that neutralize the HBGA binding sites has been largely accepted as a surrogate marker for efficacy and correlates well with protection in humans and chimpanzees [17, 37, 38]. The present disclosure demonstrates that the GELVAC vaccine powder containing either GI or GII VLPs administered intranasally was capable of producing antibodies in guinea pigs that inhibited the binding of the VLPs to pig gastric mucin. The serum levels of these neutralizing antibodies were correlated with the amount of GI or GII VLP administered to the guinea pigs. In a similar fashion that was observed for serum IgG antibodies, a boosting effect in the neutralizing antibody titers after the second dose was also observed. However, a larger amount of VLP antigen was required for the production of neutralizing antibodies as compared to the induction of total specific IgG antibodies. A dose of 15 μg for both GI and GII VLP antigen was required to maximize the production of neutralizing antibodies. These results correlated well with the serum IgG titers and further support a maximally efficacious dose of 15 μg for each genogroup. A dose of the vaccine which corresponds to at least >100-fold increase in antigen-specific IgG titers and >5-fold increase in neutralizing antibody titers is considered effective to confer active immunity against a norovirus infection.

Mucosal Antibody Response

To investigate the mucosal immune response at various antigen doses, mucosal antibody titers were evaluated in the reproductive tracts with vaginal lavage (FIG. 9). GI vaginal antibody titers were elevated in 50 μg dose group by day 21 and in all dose groups greater than 1 μg by day 56. GII vaginal antibody titers were elevated in the 5 μg, 50 μg, and 100 μg dose groups by day 42. The lowest dose that elicited a mucosal IgG response was 5 μg for both GI and GII. The highest vaginal antibody titers occurred at 15 μg for GI and 100 μg for GII. These results showed that vaginal IgG antibody titers exhibited a dose-dependent response that reached a significantly higher level at 15 μg and 50 μg for GI and GII, respectively.

Antigen specific IgG antibody production in the vaginal tract showed similar trends to what was observed for both antigen specific IgG antibodies and neutralizing antibodies detected in serum. Presence of mucosal IgG antibodies is most likely conferred through transudation of serum IgG antibodies [39]. These results demonstrate that the GELVAC vaccine powder is capable to inducing a mucosal response along with a neutralizing antibody response.

Example 4

Immunizations Via Both Mucosal and Parenteral Routes

Figure 10:
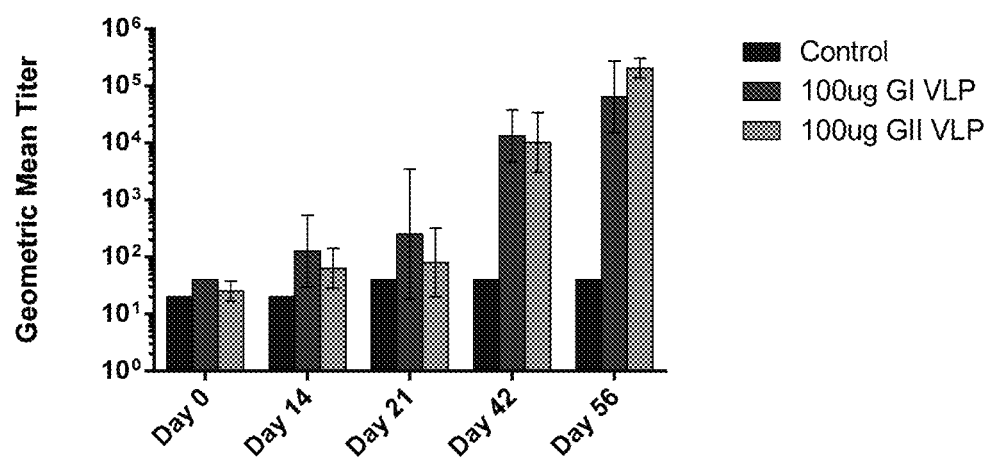
FIG. 10: Serum and vaginal norovirus specific IgG production after 2 intranasal immunizations on day 0 and 21 followed by a parenteral immunization on day 42 of GELVAC vaccine powder. Female Hartley guinea pigs were immunized intranasally with 20 mg of powder formulation containing 100 μg of either GI or GII.4 VLP on days 0 and 21. On day 42, animals were immunized via an intramuscular (IM) injection of 20 mg of powder formulation containing 100 μg of GI or GII.4 VLP following reconstitution with water. Vaginal lavages samples were collected on days 0, 14, 21, 42, and 56 and analyzed for Norovirus VLP specific IgG antibodies in serum (A) and Norovirus VLP specific IgG antibodies from vaginal swabs derived (B). *$P<0.05$ as compared to the placebo control group.
Figure 10:
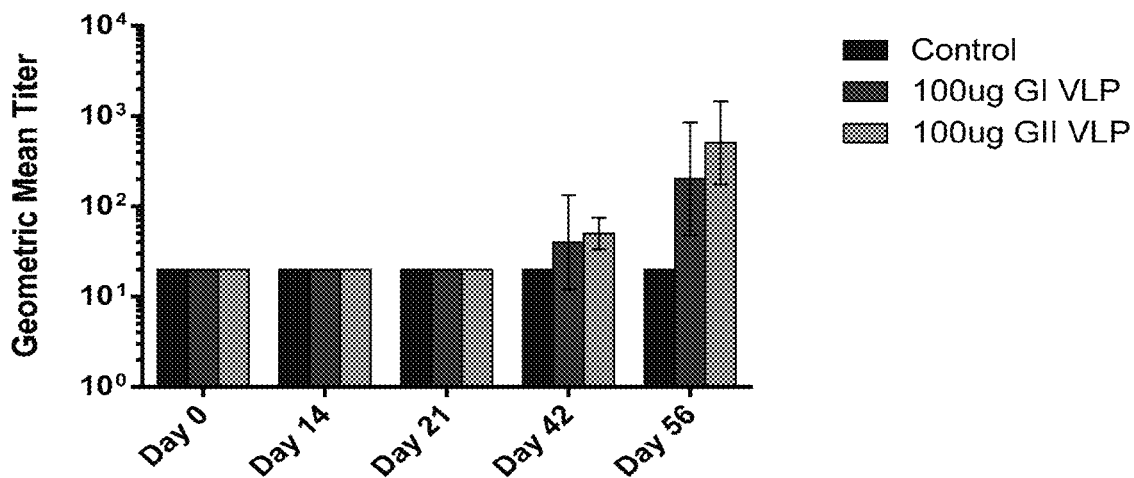

Animals received the first two doses of GELVAC norovirus VLP powder vaccine containing GI or GII. 4 VLP intranasally as described above on days 0 and 21. For the third dose, the same amount of the vaccine powders were reconstituted with water and administered by intramuscular (IM) injection on day 42. The serum and vaginal antibodies were measured as described above. As shown in FIG. 10, the total antigen specific IgG antibodies present in the serum and vaginal lavage increased with the monovalent GI and GII vaccine powders. The monovalent powder vaccines used in this experiment were manufactured with either GI or GII norovirus VLPs. Compared to the control group, serum IgG titers increased on day 21 and were higher on day 42. By day 42, serum IgG titers increased by >200-fold for both GI and GII antigens.

Serum VLP specific titers further increased by an additional 10-fold after the IM immunization for both GI and GII (FIG. 10). VLP specific IgG titers were also further increased in the vaginal lavage samples. At day 42, following two IN immunizations, 2- to 4-fold increases in antigen specific IgG titers were observed in the vaginal lavage for both GI and GII VLPs. Following the IM immunization, VLP specific titers in vaginal lavage increased by 10-fold for both GI and GII VLPs. Thus, a relatively larger increase in the mucosal antibodies was obtained after the IM immunization. These results showed that the norovirus VLPs formulation with GELVAC nasal powder were highly immunogenic and capable of inducing significant systemic and mucosal antibody production following mucosal or intranasal immunization, and importantly, both systemic and mucosal antibody responses can be further increased by an additional parenteral or IM immunization The present disclosure further shows that immune responses induced by a norovirus vaccine can be further enhanced by immunization via both parenteral and mucosal routes. As shown herein, animals were first immunized with the norovirus VLP powder vaccine intranasally twice followed by an additional immunization via IM injection with the reconstituted powder vaccine, and a significant increase in both systemic and mucosal immune responses was obtained after the additional immunization by IM injection. Thus, a norovirus vaccine can be administered with one or more doses via a mucosal route followed by one or more doses via a parenteral route or vice versa to further enhance the immune responses. There may be an interval of 2 to 4 weeks between the two routes of immunization. It is preferred that the first dose is administered by the mucosal route and the second dose by the parenteral route. The dry powder vaccine is particularly advantageous for immunization by the combinatorial routes, i.e., the mucosal immunization can be performed directly with the dry powder vaccine by intranasal delivery, whereas the parenteral immunization by IM injection is performed with the same dry powder vaccine after reconstitution, which may simply be carried out with sterile water.

Example 5

Immunizations with Bivalent Vaccines

Immunogenicity of GelVac GI and GII Powders

The immunogenicity of the GELVAC vaccine powder formulated with GI and GII VLPs, individually, has been reported previously [14, 16]. To further these studies, dose-dependent immune responses were investigated with bivalent GELVAC vaccine formulations containing GI and GII norovirus VLPs. Animals were dosed with varying amounts of the bivalent norovirus GI and GII VLPs (Table 4) on days 0 and 21. Serum and vaginal lavage samples were collected from the animals on days 0 (preimmunization), 21, 42 and 56. Intestinal lavage was collected after the termination of the study (day 56).

TABLE 4

Bivalent Vaccine Animal Experimental Design

| Group | Formulation | rVLP Dose (μg)* | Antigen Presentation Schedule (Study Day) | Sample Collection Schedule (Study Day) | Group Size (n) |
|---|---|---|---|---|---|
| 1 | Control | 0 | 0, 21 | 0, 7, 14, 21, 42, 56 | 4 |
| 2 | GI Antigen | 50 | 0, 21 | 0, 7, 14, 21, 42, 56 | 4 |
| 3 | GII Antigen | 50 | 0, 21 | 0, 7, 14, 21, 42, 56 | 4 |
| 4 | GI & GII Antigen | 5 | 0, 21 | 0, 7, 14, 21, 42, 56 | 4 |
| 5 | GI & GII Antigen | 15 | 0, 21 | 0, 7, 14, 21, 42, 56 | 4 |
| 6 | GI & GII Antigen | 50 | 0, 21 | 0, 7, 14, 21, 42, 56 | 4 |
| 7 | GI & GII Antigen | 100 | 0, 21 | 0, 7, 14, 21, 42, 56 | 4 |

*Animals were immunized with a total of 20 mg of powder via both nares. Each nare received 10 mg of powder or half of the total antigen dose.

Serum Antibody Response

Figure 11:
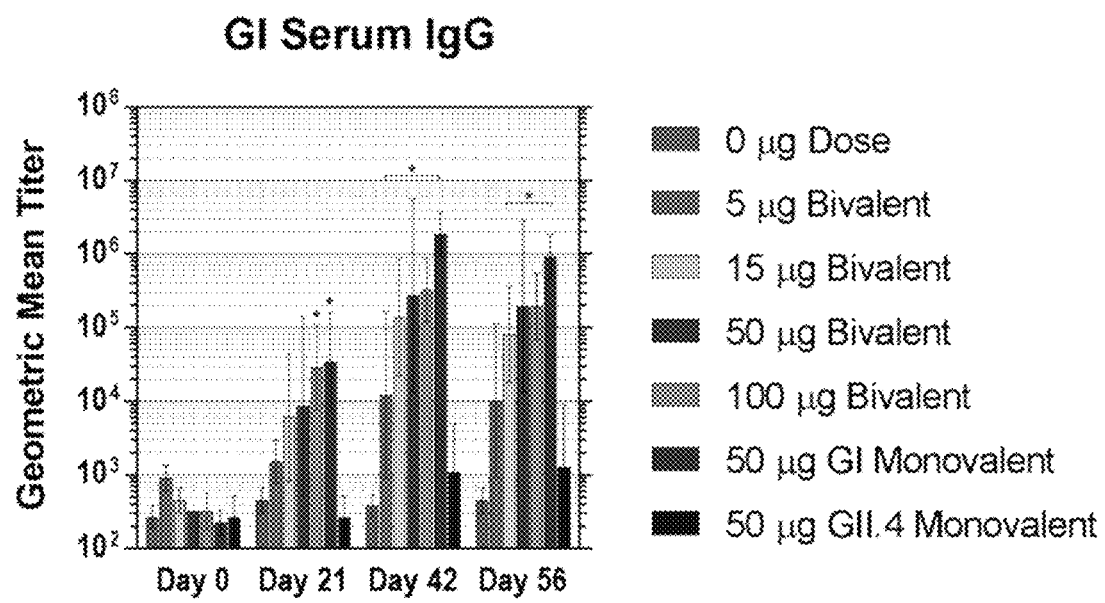
FIG. 11: Serum norovirus-specific IgG and IgA production following intranasal immunization with GELVAC monovalent and bivalent vaccine powders. Female Hartley guinea pigs were immunized intranasally with 20 mg of a bivalent vaccine powder formulation containing various amounts of GI and GII.4 VLPs on days 0 and 21. Serum samples were collected on day 0, 14, 21, 42, and 56 and analyzed for specific IgG antibodies against GI (A) and GII.4 (B). Serum samples were also analyzed for specific IgA antibodies against GI (C) and GII.4 (D). Error bars are provided as geometric standard error. *$p<0.05$ as compared to the placebo control group.
Figure 11:
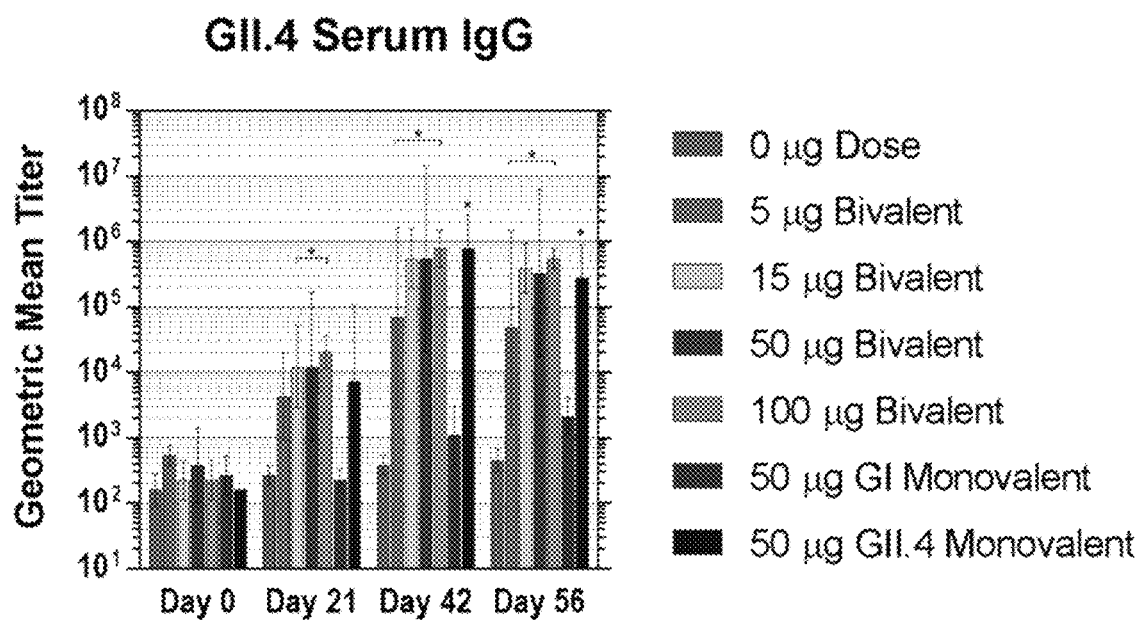
Figure 11:
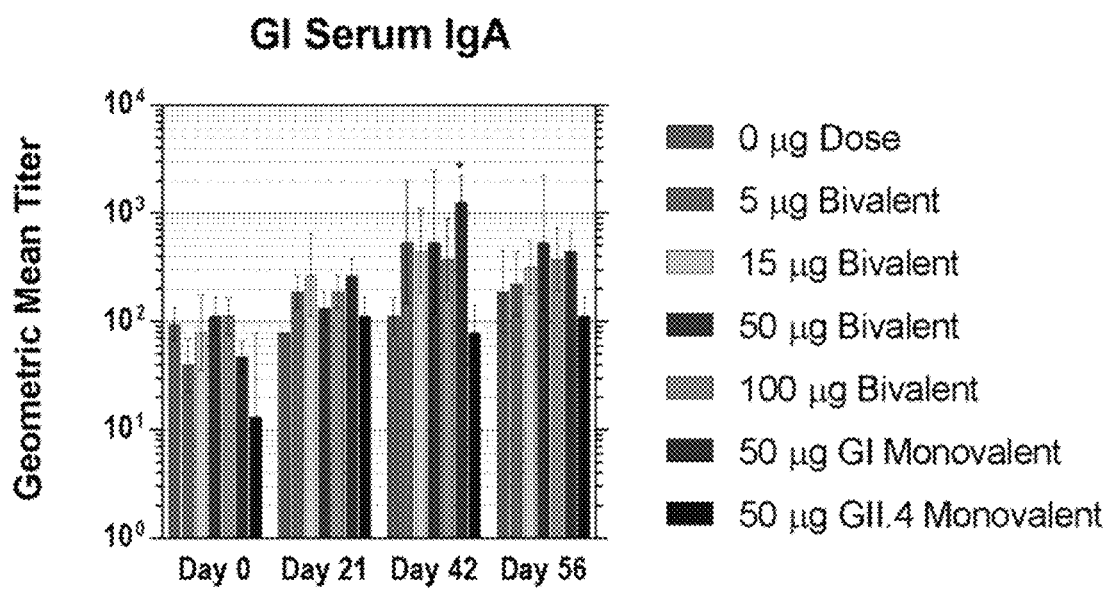
Figure 11:
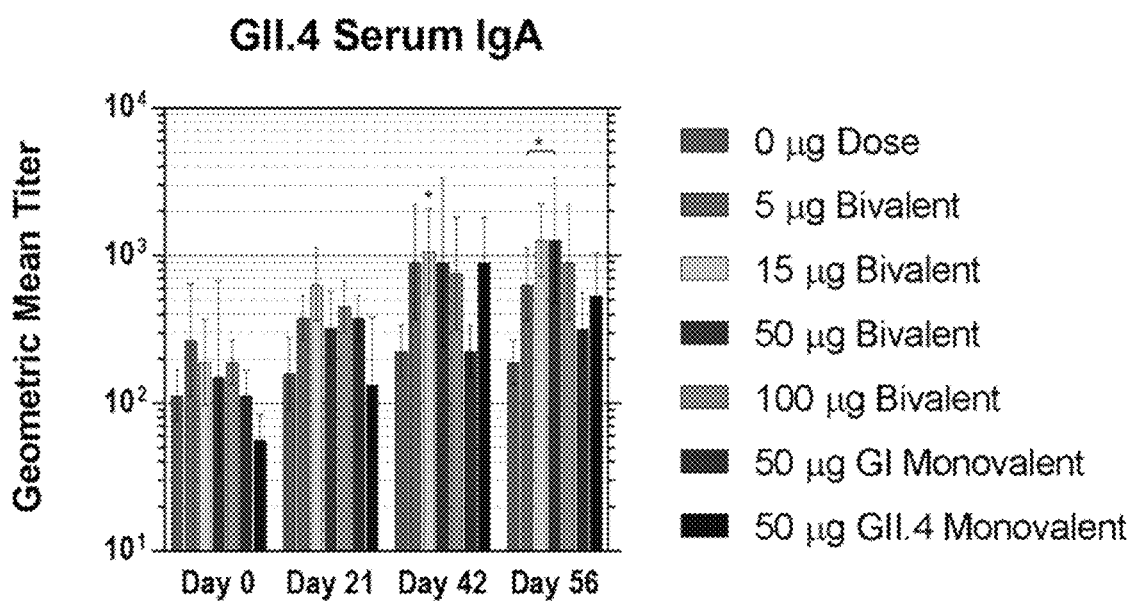

Serum samples were analyzed for norovirus VLP specific IgG by ELISA. The total antigen specific IgG antibodies present in the serum exhibited a dose-dependent increase with both GI and GII vaccine powders (FIG. 11). Compared to the control group, serum IgG titers increased on day 14 and a further increase was observed on days 21 and 42 at all doses >5 μg. By day 14, GI IgG titers increased by at >4-fold compared to controls. Further increases in GI IgG titers were observed at day 21 compared to day 14. Similar results were observed for GII IgG titers at day 14 and 21. At day 42 GI IgG titers increased by >600-fold compared to day 21 for all dose groups of ≥5 μg and GII IgG titers increased by >300-fold compared to day 21 for all dose groups of ≥5 μg. There were no significant differences between 15 μg and 100 μg doses for GI and between 5 μg and 100 μg doses for GII. The lowest dose that elicited an antigen specific IgG response was 5 μg for both GI and GII which corresponded to a titer of 30800 and 245840 on day 56, respectively. Antigen specific IgA serum levels were also investigated. At day 56, anti-GI and anti-GII VLP IgA antibodies were observed at all doses that were administered when compared to the mock dose controls (FIG. 11). They also exhibited an overall trend of higher levels at higher antigen doses.

Figure 12:
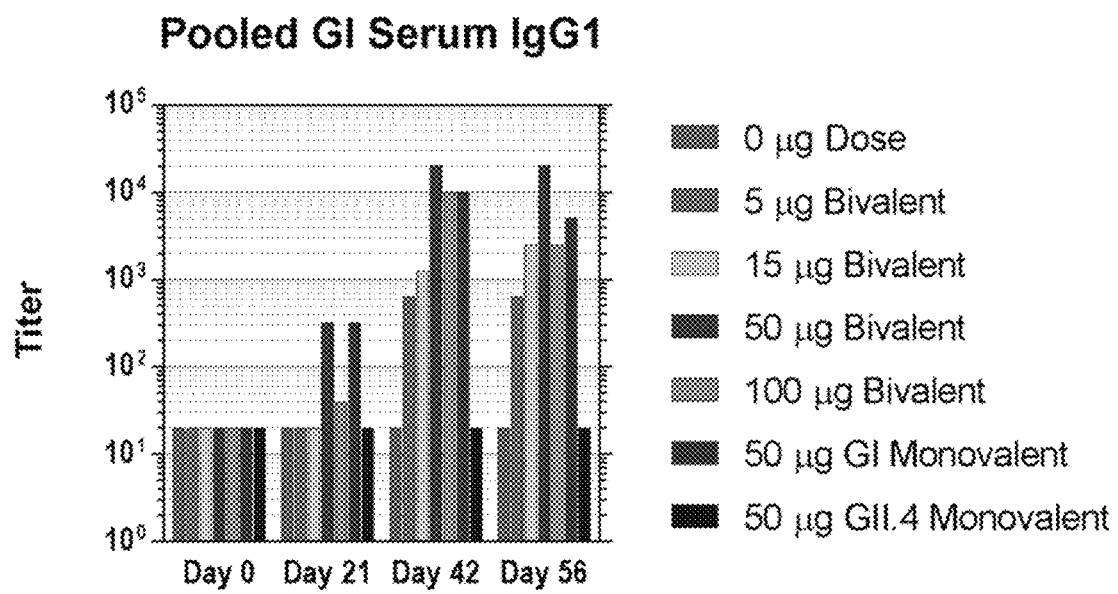
FIG. 12: Serum norovirus-specific IgG1 and IgG2 production following intranasal administration with GELVAC dry powder monovalent and bivalent vaccine. Serum samples were analyzed for norovirus-specific IgG1 antibodies against GI (A) and GII.4 (B), and norovirus-specific IgG2 antibodies against GI (C) and GII.4 (D).
Figure 12:
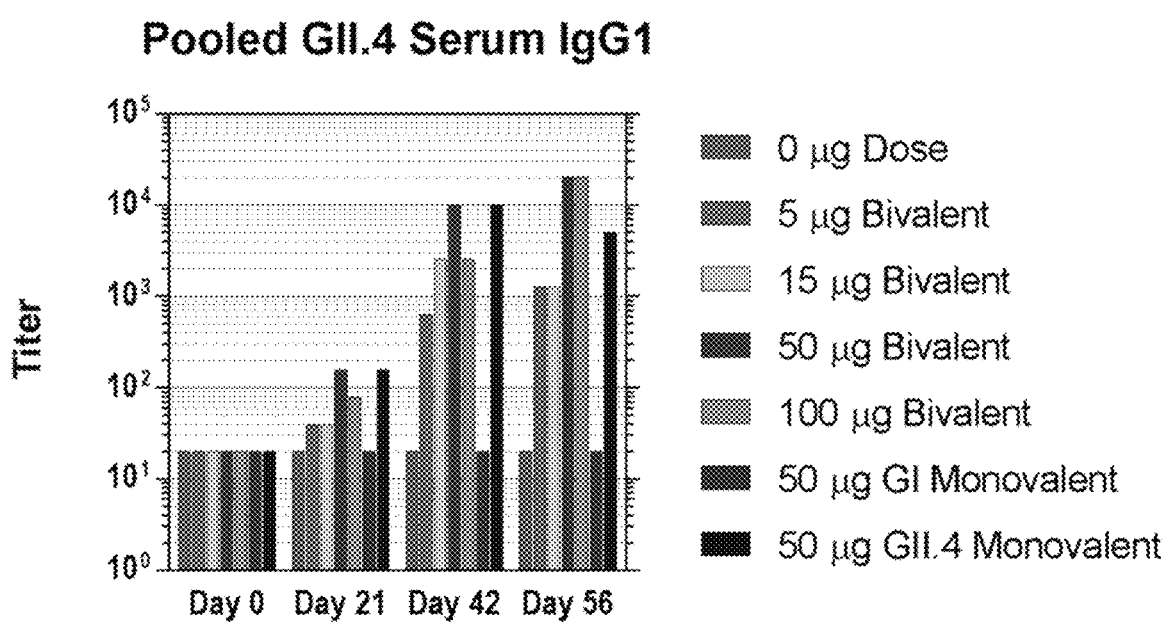
Figure 12:
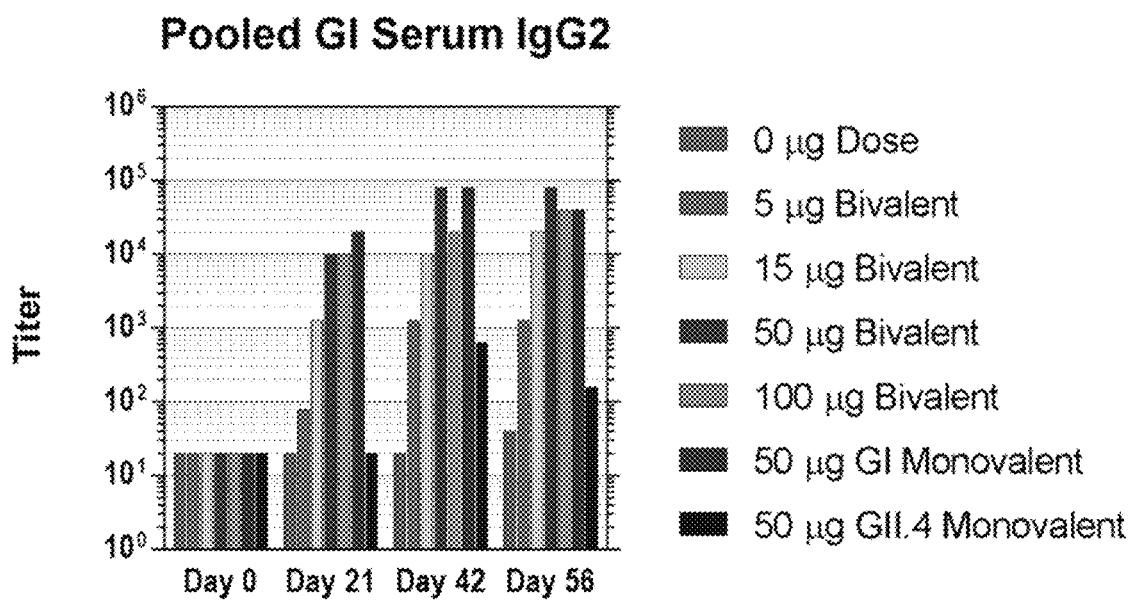
Figure 12:
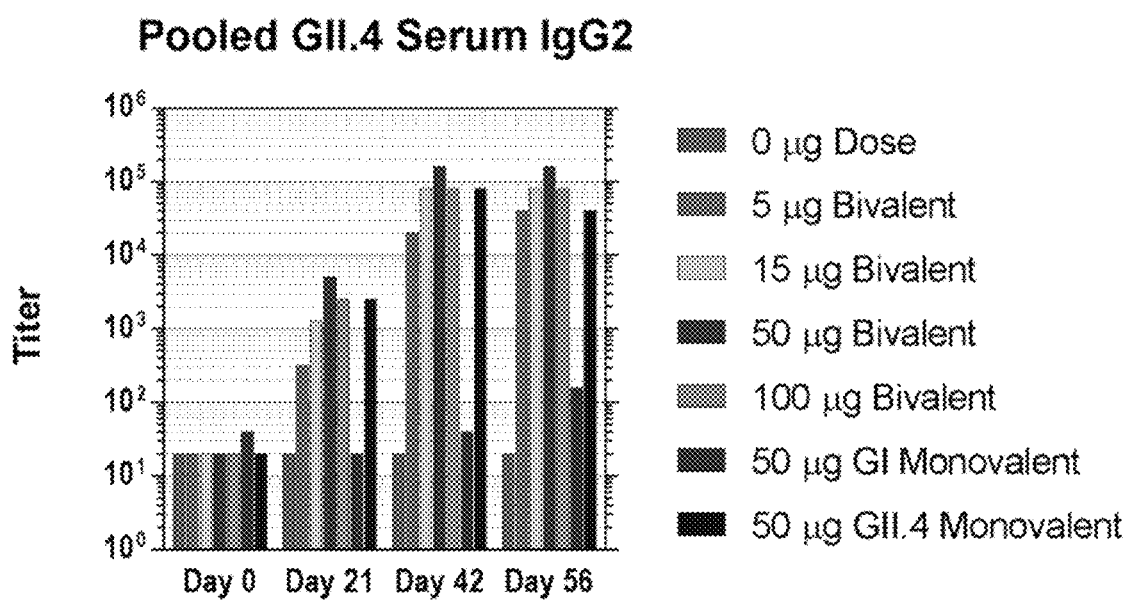

The IgG1 and IgG2 subclasses were also analyzed using the pooled serum samples from each group (FIG. 12). As shown, GI and GII IgG2 specific antibody titers were observed at day 14 but not IgG1 specific titers. GI and GII IgG2 specific titers were also shown to be higher than GI or GII IgG1 specific titers at day 21. IgG1 and IgG2 Boosting effects were also observed for both GI and GII at day 42. Overall, the IgG2 titers were higher than IgG1 titers for both GI and GII VLPs (FIG. 12). These results show that the bivalent GI/GII VLP vaccine formulations were highly immunogenic and capable of producing a wide range of antibody responses.

Serum Neutralization Antibody Response

Figure 13:
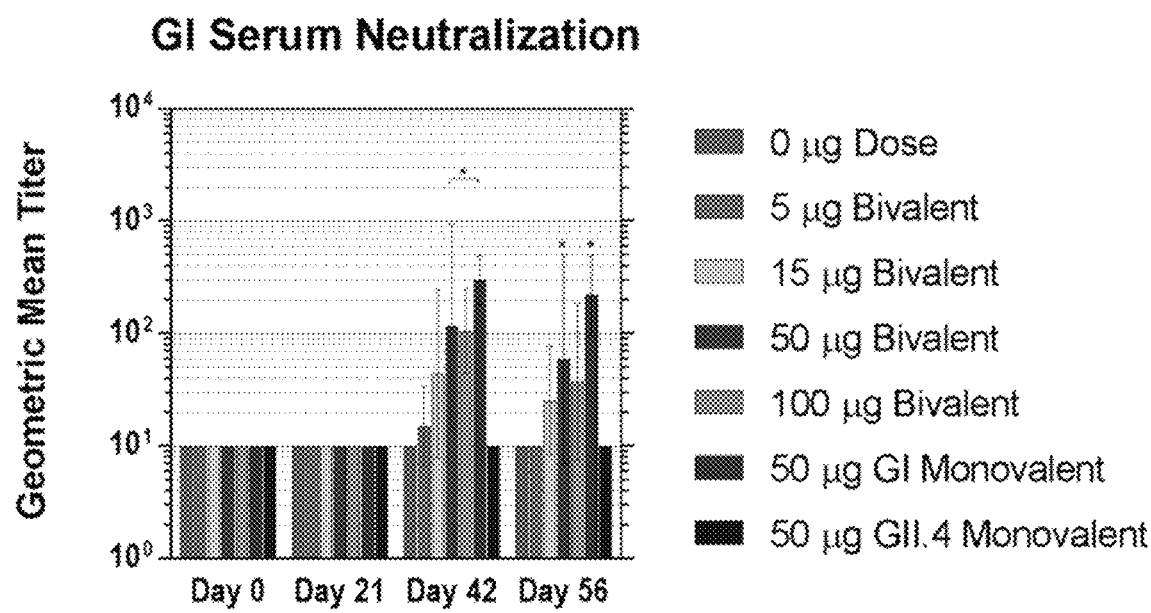
FIG. 13: Neutralizing antibody production following intranasal immunization with GELVAC dry powder monovalent and bivalent vaccine. Female Hartley guinea pigs were immunized intranasally with 20 mg of a bivalent vaccine powder formulation containing various amounts of GI and GII.4 VLPs on days 0 and 21. Serum samples were collected on days 0, 14, 21, 42, and 56 and analyzed for GI (A) and GII.4 (B) neutralizing antibodies. Error bars are provided as geometric standard error. *$p<0.05$ as compared to the placebo control group.
Figure 13:
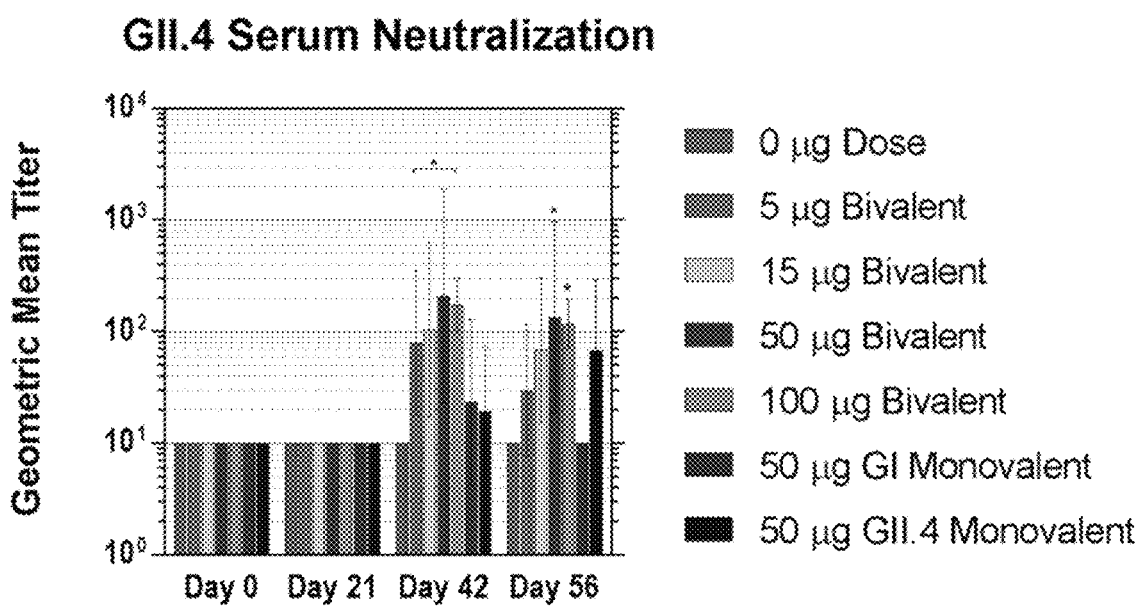

Antigen specific antibodies were investigated for their ability to inhibit the binding of the norovirus VLPs to porcine gastric mucin. The neutralizing antibodies present in the serum exhibited a dose-dependent response similar to that observed for antigen specific IgG antibody titers (FIG. 13). Compared to the control, GI neutralizing antibody titers were elevated in the 15 µg, 50 µg, and 100 µg dose groups by day 42 with similar titers observed at day 56. GII neutralizing antibody titers were elevated for all groups by day 42 with similar titers observed at day 56. By day 42, GI neutralizing antibody titers increased by >50-fold for all dose groups ≥15 µg and GII neutralizing antibody titers increased by >190-fold for all dose groups ≥5 µg, consistent with the findings with serum IgG titers. There were no significant differences between 5 µg and 100 µg doses for both GI and GII at day 56. The lowest dose that produced a detectable neutralization titer at day 56 was 15 µg for GI and 5 µg for GII. These results showed that the neutralizing antibody titers followed a similar dose-dependent response to that observed for the total serum IgG titers.

Mucosal Antibody Response

Figure 14:
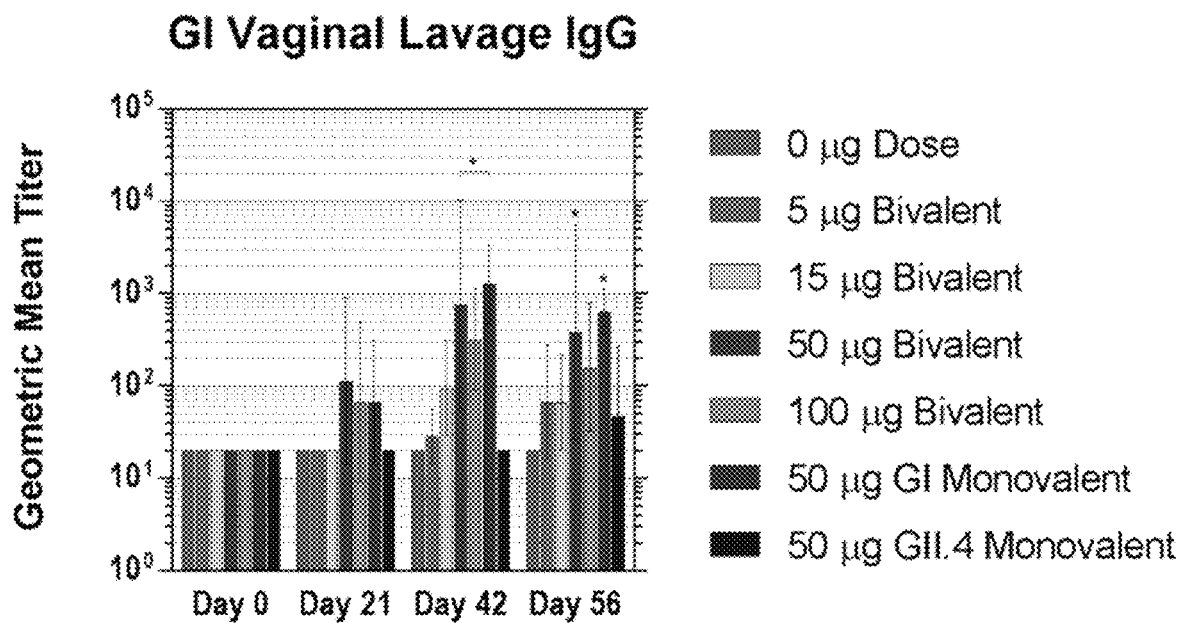
FIG. 14: Mucosal norovirus-specific antibody production following intranasal immunization with GELVAC dry monovalent and powder bivalent vaccine. Female Hartley guinea pigs were immunized intranasally with 20 mg of a bivalent vaccine powder formulation containing various amounts of GI and GII.4 VLPs on days 0 and 21. Vaginal lavage samples were collected on days 0, 14, 21, 42, and 56 and analyzed for GI (A) and GII.4 (B) norovirus-specific antibodies. On day 56, animals were euthanized and intestinal lavage samples were analyzed for GI (C) and GII.4 (D) norovirus-specific antibodies. Error bars are provided as geometric standard error. *p<0.05 as compared to the placebo control group.
Figure 14:
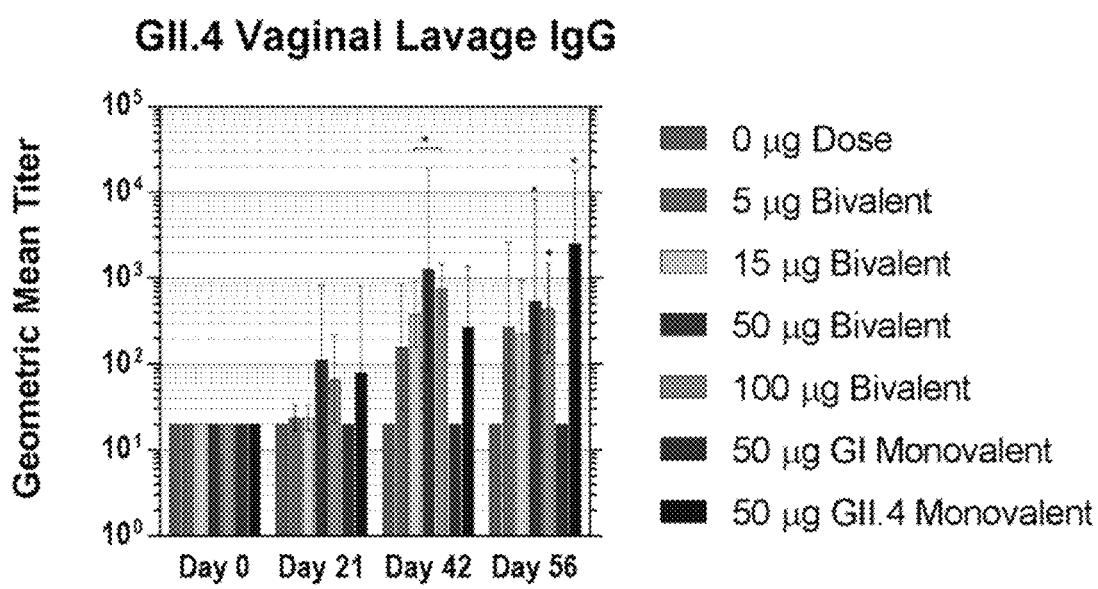
Figure 14:
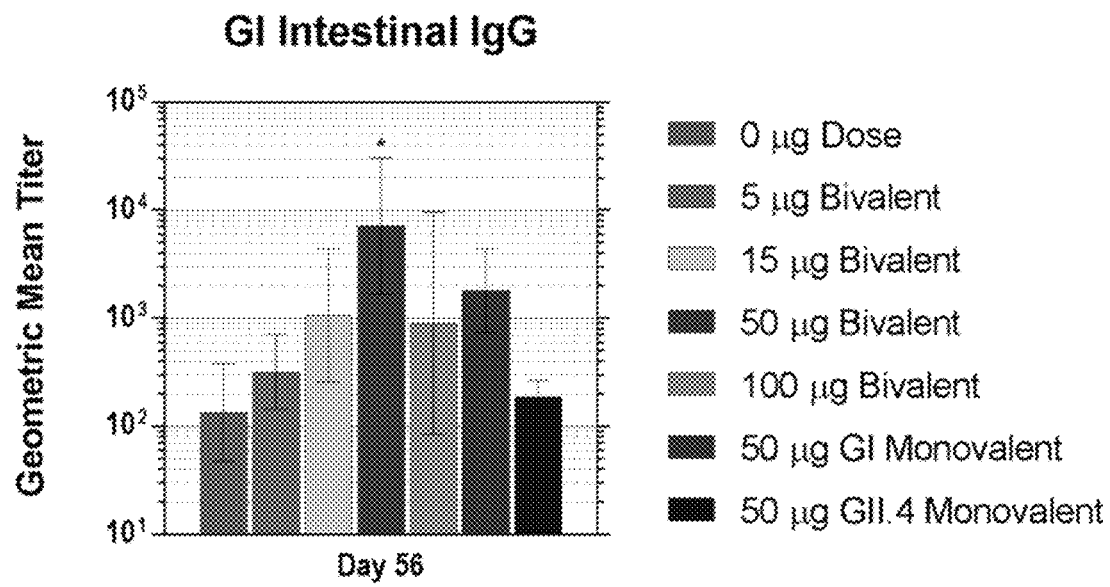
Figure 14:
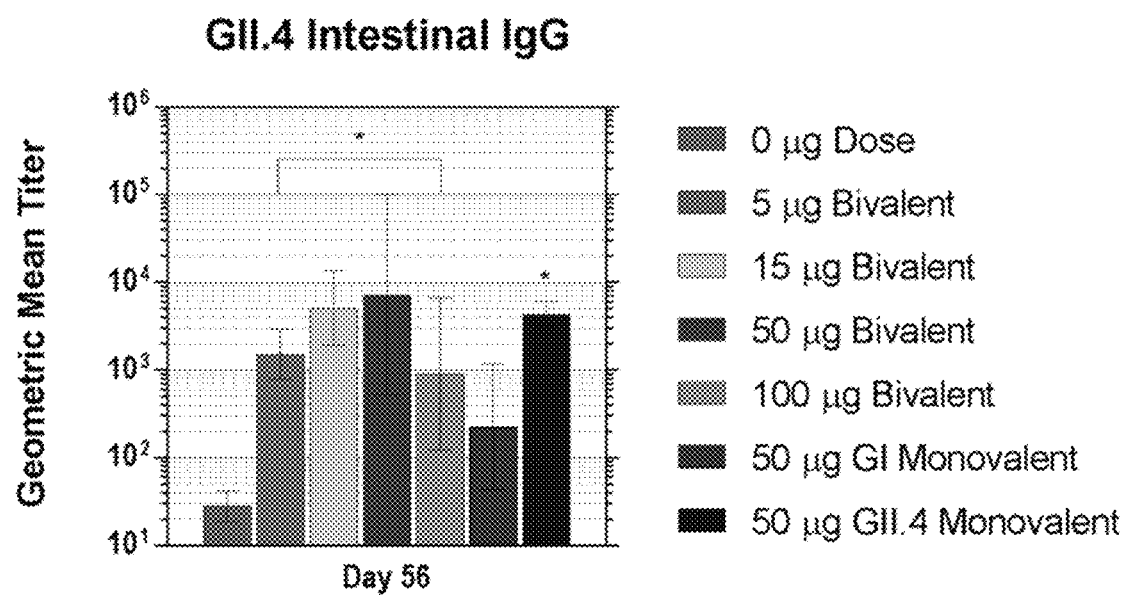

To investigate the mucosal immune response at various antigen doses, mucosal antibody titers were evaluated in the reproductive tracts and intestines (FIG. 14). GI vaginal antibody titers were elevated in 50 µg and 100 µg dose group by day 21 and in all dose groups greater than 5 µg by day 56. GII vaginal antibody titers were elevated in the 5 µg, 15 µg, 50 µg, and 100 µg dose groups by day 42. The lowest dose that elicited a mucosal IgG response was 5 µg for both GI and GII. The highest vaginal antibody titers occurred at 50 µg for both GI and GII. These results showed that vaginal IgG antibody titers exhibited a dose-dependent response. GI and GII specific IgG titers were also observed in the intestines at day 56 (FIGS. 14 C and D). As shown, antibody titers were observed in all treatment groups for both GI and GII specific antibodies.

REFERENCES CITED

[1] Hedberg C. Food-related illness and death in the United States. Emerg Infect Dis. 1999; 5:840-2.

[2] Hall A J, Lopman B A, Payne D C, Patel M M, Gastanaduy P A, Vinjé J, et al. Norovirus disease in the United States. Emerg Infect Dis. 2013; 19:1198-205.

[3] Mead P S, Slutsker L, Griffin P M, Tauxe R V. Food-related illness and death in the united states reply to dr. hedberg. Emerg Infect Dis. 1999; 5:841-2.

[4] Patel M M, Widdowson M A, Glass R I, Akazawa K, Vinje J, Parashar U D. Systematic literature review of role of noroviruses in sporadic gastroenteritis. Emerg Infect Dis. 2008; 14:1224-31.

[5] Yun S I, Kim J K, Song B H, Jeong A Y, Jee Y M, Lee C H, et al. Complete genome sequence and phylogenetic analysis of a recombinant Korean norovirus, CBNU1, recovered from a 2006 outbreak. Virus Res. 2010; 152: 137-52.

[6] Lindesmith L C, Costantini V, Swanstrom J, Debbink K, Donaldson E F, Vinjé J, et al. Emergence of a norovirus GII strain correlates with changes in evolving blockade epitopes. J Virol. 2013; 87:2803-13.

[7] Caul E O. Small round structured viruses: airborne transmission and hospital control. Lancet. 1994; 343: 1240-2.

[8] Blanton L H, Adams S M, Beard R S, Wei G, Bulens S N, Widdowson M A, et al. Molecular and epidemiologic trends of caliciviruses associated with outbreaks of acute gastroenteritis in the United States, 2000-2004. J Infect Dis. 2006; 193:413-21.

[9] Fankhauser R L, Monroe S S, Noel J S, Humphrey C D, Bresee J S, Parashar U D, et al. Epidemiologic and molecular trends of "Norwalk-like viruses" associated with outbreaks of gastroenteritis in the United States. J Infect Dis. 2002; 186:1-7.

[10] Zheng D P, Widdowson M A, Glass R I, Vinjé J. Molecular epidemiology of genogroup II-genotype 4 noroviruses in the United States between 1994 and 2006. J Clin Microbiol. 2010; 48:168-77.

[11] Donaldson E F, Lindesmith L C, Lobue A D, Baric R S. Norovirus pathogenesis: mechanisms of persistence and immune evasion in human populations. Immunol Rev. 2008; 225:190-211.

[12] LoBue A D, Lindesmith L, Yount B, Harrington P R, Thompson J M, Johnston R E, et al. Multivalent norovirus vaccines induce strong mucosal and systemic blocking antibodies against multiple strains. Vaccine. 2006; 24:5220-34.

[13] Sundararajan A, Sangster M Y, Frey S, Atmar R L, Chen W H, Ferreira J, et al. Robust mucosal-homing antibody-secreting B cell responses induced by intramuscular administration of adjuvanted bivalent human norovirus-like particle vaccine. Vaccine. 2015; 33:568-76.

[14] Herbst-Kralovetz M, Mason H S, Chen Q. Norwalk virus-like particles as vaccines. Expert Rev Vaccines. 2010; 9:299-307.

[15] Tacket C O, Sztein M B, Losonsky G A, Wasserman S S, Estes M K. Humoral, mucosal, and cellular immune responses to oral Norwalk virus-like particles in volunteers. Clin Immunol. 2003; 108:241-7.

[16] Atmar R L, Bernstein D I, Harro C D, Al-Ibrahim M S, Chen W H, Ferreira J, et al. Norovirus vaccine against experimental human Norwalk Virus illness. N Engl J Med. 2011; 365:2178-87.

[17] Reeck A, Kavanagh O, Estes M K, Opekun A R, Gilger M A, Graham D Y, et al. Serological correlate of protection against norovirus-induced gastroenteritis. J Infect Dis. 2010; 202:1212-8.

[18] Santi L, Huang Z, Mason H. Virus-like particles production in green plants. Methods. 2006; 40:66-76.

[19] White L J, Hardy M E, Estes M K. Biochemical characterization of a smaller form of recombinant Norwalk virus capsids assembled in insect cells. J Virol. 1997; 71:8066-72.

[20] Velasquez L S, Shira S, Berta A N, Kilbourne J, Medi B M, Tizard I, et al. Intranasal delivery of Norwalk virus-like particles formulated in an in situ gelling, dry powder vaccine. Vaccine. 2011; 29:5221-31.

[21] Parra G I, Bok K, Taylor R, Haynes J R, Sosnovtsev S V, Richardson C, et al. Immunogenicity and specificity of norovirus Consensus GII virus-like particles in monovalent and bivalent vaccine formulations. Vaccine. 2012; 30:3580-6.

[22] Ni YaY, K. M. In-situ Gel Formation of Pectin. In: USPTO, editor. United States: Carrington Laboratories, Inc.; 2004.

[23] Santi L, Batchelor L, Huang Z, Hjelm B, Kilbourne J, Arntzen C J, et al. An efficient plant viral expression system generating orally immunogenic Norwalk virus-like particles. Vaccine. 2008; 26:1846-54.

[24] Biggar K K, Dawson N J, Storey K B. Real-time protein unfolding: a method for determining the kinetics of native protein denaturation using a quantitative real-time thermocycler. Biotechniques. 2012; 53:231-8.

[25] Lindesmith L C, Debbink K, Swanstrom J, Vinjé J, Costantini V, Baric R S, et al. Monoclonal antibody-based antigenic mapping of norovirus GII-2002. J Virol. 2012; 86:873-83.

[26] Koho N M, Mykkanen A K, Reeben M, Raekallio M R, lives M, Poso A R. Sequence variations and two levels of MCT1 and CD147 expression in red blood cells and gluteus muscle of horses. Gene. 2012; 491:65-70.

[27] Koho T, Mantyla T, Laurinmaki P, Huhti L, Butcher S J, Vesikari T, et al. Purification of norovirus-like particles (VLPs) by ion exchange chromatography. Journal of virological methods. 2012; 181:6-11.

[28] Harrington P R, Lindesmith L, Yount B, Moe C L, Baric R S. Binding of Norwalk virus-like particles to ABH histo-blood group antigens is blocked by antisera from infected human volunteers or experimentally vaccinated mice. J Virol. 2002; 76:12335-43.

[29] Marionneau S, Ruvoen N, Le Moullac-Vaidye B, Clement M, Cailleau-Thomas A, Ruiz-Palacois G, et al. Norwalk virus binds to histo-blood group antigens present on gastroduodenal epithelial cells of secretor individuals. Gastroenterology. 2002; 122:1967-77.

[30] Hansman G S, Natori K, Shirato-Horikoshi H, Ogawa S, Oka T, Katayama K, et al. Genetic and antigenic diversity among noroviruses. The Journal of general virology. 2006; 87:909-19.

[31] Parker T D, Kitamoto N, Tanaka T, Hutson A M, Estes M K. Identification of Genogroup I and Genogroup II broadly reactive epitopes on the norovirus capsid. J Virol. 2005; 79:7402-9.

[32] Czako R, Atmar R L, Opekun A R, Gilger M A, Graham D Y, Estes M K. Experimental human infection with Norwalk virus elicits a surrogate neutralizing antibody response with cross-genogroup activity. Clinical and vaccine immunology: CVI. 2015; 22:221-8.

[33] Atmar R L, Opekun A R, Gilger M A, Estes M K, Crawford S E, Neill F H, et al. Determination of the 50% human infectious dose for Norwalk virus. J Infect Dis. 2014; 209:1016-22.

[34] Lindesmith L C, Ferris M T, Mullan C W, Ferreira J, Debbink K, Swanstrom J, et al. Broad Blockade Antibody Responses in Human Volunteers after Immunization with a Multivalent Norovirus VLP Candidate Vaccine: Immunological Analyses from a Phase I Clinical Trial. PLoS Med. 2015; 12:e1001807.

[35] Bernstein D I, Atmar R L, Lyon G M, Treanor J J, Chen W H, Jiang X, et al. Norovirus Vaccine Against Experimental Human GII Virus Illness: A Challenge Study in Healthy Adults. J Infect Dis. 2015; 211:870-8.

[36] Treanor J J, Atmar R L, Frey S E, Gormley R, Chen W H, Ferreira J, et al. A novel intramuscular bivalent norovirus virus-like particle vaccine candidate—reactogenicity, safety, and immunogenicity in a phase 1 trial in healthy adults. J Infect Dis. 2014; 210:1763-71.

[37] Bok K, Parra G I, Mitra T, Abente E, Shaver C K, Boon D, et al. Chimpanzees as an animal model for human norovirus infection and vaccine development. Proc Natl Acad Sci USA. 2011; 108:325-30.

[38] Atmar R L, Bernstein D I, Lyon G M, Treanor J J, A l-Ibrahim M S, Graham D Y, et al. Serological Correlates of Protection against a GII Norovirus. Clinical and vaccine immunology: CVI. 2015{Lindesmith, 2012 #52}.

[39] Plotkin S A, Orenstein W A, Offit P A. Vaccines. 5th ed. Philadelphia, Pa.: Saunders/Elsevier; 2008.

[40] Karst S M. Pathogenesis of Noroviruses, Emerging RNA Viruses. Viruses 2010; 2:748-781.

[41] Centers for Disease Control and Prevention. www.cdc.gov/norovirus.

[42] Varshney D, Singh M. Lyophilized Biologics and Vaccines: Modality-Based Approaches. New York, N.Y.: Springer; 2015.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of immunizing a mammalian subject against a norovirus infection with a multivalent norovirus dry powder vaccine composition comprising a norovirus genogroup GI virus-like particle (VLP) antigen, a norovirus genogroup GII VLP antigen, and an anionic polysaccharide, the method comprising:
administering, to the mammalian subject, a first dose of the dry powder vaccine composition by a mucosal route, thereby initiating an immune response against a norovirus antigen, wherein the first dose comprises about 50 micrograms of the norovirus genogroup GI VLP antigen and the norovirus genogroup GII VLP antigen, and
administering, to the mammalian subject, a second dose of the dry powder vaccine composition by the mucosal route at least 2 weeks after the administering the first dose, wherein the second dose comprises about 50 micrograms of the norovirus genogroup GI VLP antigen and the norovirus genogroup GII VLP antigen.

2. The method of claim 1, wherein the mucosal route is an intranasal route.

3. The method of claim 1, wherein the administering the first dose comprises administering at least 20 mg of the dry powder vaccine composition.

4. The method of claim 2, wherein the first dose and the second dose each comprise 50 micrograms of the norovirus genogroup GI VLP antigen and the norovirus genogroup GII VLP antigen.

5. The method of claim 1, wherein the composition is administered to reduce a risk of norovirus infection.

6. The method of claim 1, wherein the composition is administered to treat symptoms of norovirus infection.

7. The method of claim 1, wherein the administering the second dose occurs 2-4 weeks after the administering the first dose.

8. The method of claim 1, wherein the anionic polysaccharide is sodium polygalacturonate extracted from *Aloe vera*.

9. The method of claim 8, wherein the dry powder vaccine composition comprises at least 0.1% w/w of sodium polygalacturonate.

10. The method of claim 1, wherein a mean particle size of the dry powder vaccine composition is from about 25 micrometers to about 30 micrometers.

11. The method of claim 1, wherein a median particle size of the dry powder vaccine composition is from about 23 micrometers to about 25 micrometers.

12. The method of claim 1, wherein the first dose comprises about 20 mg of the dry powder vaccine composition.

13. The method of claim 1, wherein the second dose comprises about 20 mg of the dry powder vaccine composition.

* * * * *